(12) United States Patent
Baxter et al.

(10) Patent No.: US 12,024,504 B2
(45) Date of Patent: Jul. 2, 2024

(54) 1-METHYL-1H-PYRAZOL-3-YL DERIVATIVES FOR USE IN THE TREATMENT OF NEOVASCULAR DISEASES

(71) Applicant: EXONATE LIMITED, Duxford (GB)

(72) Inventors: Andrew Douglas Baxter, Horsham (GB); Jonathan Morris, Sydney (AU)

(73) Assignee: EXONATE LIMITED, Cambridge (GB)

( * ) Notice: Subject to any disclaimer, the term of this patent is extended or adjusted under 35 U.S.C. 154(b) by 0 days.

(21) Appl. No.: 17/817,136

(22) Filed: Aug. 3, 2022

(65) Prior Publication Data

US 2022/0411412 A1 Dec. 29, 2022

Related U.S. Application Data

(63) Continuation-in-part of application No. PCT/GB2021/051810, filed on Jul. 14, 2021.

(51) Int. Cl.
*A61K 9/00* (2006.01)
*A61P 27/02* (2006.01)
*C07D 405/14* (2006.01)

(52) U.S. Cl.
CPC .......... *C07D 405/14* (2013.01); *A61K 9/0019* (2013.01); *A61K 9/0048* (2013.01); *A61P 27/02* (2018.01)

(58) Field of Classification Search
None
See application file for complete search history.

(56) References Cited

FOREIGN PATENT DOCUMENTS

| EP | 3266446 A1 * | 1/2018 | ............ A61K 31/18 |
|---|---|---|---|
| WO | 03/012105 A2 | 2/2003 | |
| WO | 2005/063293 A1 | 7/2007 | |
| WO | 2008/110777 A2 | 9/2008 | |
| WO | 2009/106855 A1 | 9/2009 | |
| WO | 2010/058227 A2 | 11/2009 | |
| WO | 2011/148200 A1 | 12/2011 | |
| WO | 2014/060763 A1 | 4/2014 | |
| WO | 2015/159103 A1 | 10/2015 | |
| WO | 2017/064512 A1 | 4/2017 | |
| WO | WO-2017064512 A1 * | 4/2017 | ........... A61K 31/496 |
| WO | 2019/063996 A1 | 4/2019 | |

OTHER PUBLICATIONS

Amin, et al.., "WT1 Mutants Reveal SRPK1 to be a Downstream Angiogenesis Target by Altering VEGF Splicing", Cancer Cell 2011.
Anderson, et al., "A Role for Local Inflammation in the Formation of Drusen in the Aging Eye", American Journal of Ophthalmology 2002.
Bain, et al., "The selectivity of protein kinase inhibitors: a further update", Biochem J. 2007.
Bates, et al., "VEGF165b, an Inhibitory Splice Variant of Vascular Endothelial Growth Factor, Is Down-Regulated in Renal Cell Carcinoma1", Cancer Research 2002.
Batson, et al., "Development of Potent, Selective SRPK1 Inhibitors as Potential Topical Therapeutics for Neovascular Eye Disease", ACS Chem. Biol. 2017.
Beazley-Long, et al., "VEGFR2 promotes central endothelial activation and the spread of pain in inflammatory arthritis", Brain, Behavior, and Immunity 2018.
Beazley-Long, et al., "Novel mechanisms of resistance to vemurafenib in melanoma—V600E B-Raf reversion and switching VEGF-A splice isoform expression", American Journal of Cancer Research 2015.
Beazley-Long, et al., "Vascular endothelial growth factor-A165b prevents diabetic neuropathic pain and sensory neuronal degeneration", Clinical Science 2015.
Bressler, et al., "Ocular Risk Factors for Developing Neovascular AMD in the Fellow Eyes of Patients with Unilateral Neovascular AMD", IOVS 2004.
Brown, et al., "Ranibizumab versus Verteporfin for Neovascular Age-Related Macular Degeneration", New England Journal of Medicine 2006.
Brown, et al., "Ranibizumab versus Verteporfin Photodynamic Therapy for Neovascular Age-Related Macular Degeneration: Two-Year Results of the Anchor Study", Ophthalmology 2009.
Campochiaro, et al., "Adenoviral Vector-Delivered Pigment Epithelium-Derived Factor for Neovascular Age-Related Macular Degeneration: Results of a Phase I Clinical Trial ", Human Gene Therapy 2006.
Das, et al., "Angiopoietin/Tek Interactions Regulate MMP-9 Expression and Retinal Neovascularization", Laboratory Investigation 2003.
Dvorak, et al., "Vascular Permeability FactorNascular Endothelial Growth Factor, Microvascular Hyperpermeability, and Angiogenesis", American Journal of Pathology 1995.
Ferris, et al., "Age-Related Macular Degeneration and Blindness due to Neovascular Maculopathy", Archives of Ophthalmology 1984.
Fine, et al., "Age-Related Macular Degeneration", New England Journal of Medicine 2000.
Gammons, et al., "Topical Antiangiogenic SRPK1 Inhibitors Reduce Choroidal Neovascularization in Rodent Models of Exudative AMD", IOVS Sep. 2013.
GB Search Report dated Feb. 18, 2020 in GB1912449.4, 3 pages.
Good, et al., "The role of endothelin in the pathophysiology of glaucoma", Expert Opinion on Therapeutic Targets 2010.
Hastie, et al., "Assay of protein kinases using radiolabeled ATP: a protocol", Nature Protocols 2006.
Houck, et al., "The Vascular Endothelial Growth Factor Family: Identification of a Fourth Molecular Species and Characterization of Alternative Splicing of RNA", Molecular Endocrinology 1991.
Hua, et al., "Recombinant Human VEGF165b Inhibits Experimental Choroidal Neovascularization", IOVS 2010.

(Continued)

*Primary Examiner* — Gigi G Huang
(74) *Attorney, Agent, or Firm* — Berg Hill Greenleaf Ruscitti LLP

(57) ABSTRACT

Anti-angiogenic treatments and compounds for use in anti-angiogenic treatments, particularly of conditions associated with abnormal angiogenesis or abnormal over-production of pro-angiogenic VEGFxxx isoforms in or on the eye are described.

3 Claims, 8 Drawing Sheets

(56) References Cited

OTHER PUBLICATIONS

ISR and Written Opinion dated Sep. 27, 2021 in PCT Application No. PCT/GB2021/051810, 12 pages.
Jager, et al., "Risks of Intra Vitreous Injection: a Comprehensive Review", Retina—the Journal of Retinal and Vitreous Diseases 2004.
Jingjing, et al., "Human Miiller Cells Express VEGF183, a Novel Spliced Variant of Vascular Endothelial Growth Factor", IOVS 1999.
Leung, et al., "Vascular Endothelial Growth Factor Is a Secreted Angiogenic Mitogen", Science 1989.
Magnussen, et al., "VEGF-A165b Is Cytoprotective and Antiangiogenic in the Retina", IOVS 2010.
Mineur, et al., "Newly identified biologically active and proteolysis-resistant VEGF-A isoform VEGF111 is induced by genotoxic agents", Journal of Cell Biology 2007.
Nowak, et al., "Expression of pro- and anti-angiogenic isoforms of VEGF is differentially regulated by splicing and growth factors", Journal of Cell Science 2008.
Nowak, et al., "Regulation of Vascular Endothelial Growth Factor (VEGF) Splicing from Pro-angiogenic to Anti-angiogenic Isoforms", Journal of Biological Chemistry 2010.
Patz, et al., "Diseases of the macula: the diagnosis and management of choroidal heovascularization", Transactions American Academy of Ophthalmology and Otolaryngology 1977.
Perrin, et al., "Diabetic retinopathy is associated with a switch in splicing from anti- to pro-angiogenic isoforms of vascular endothelial growth factor", Diabetologia 2005.

Pritchard-Jones, et al., "Expression of VEGFxxxb, the inhibitory isoforms of VEGF, in malignant melanoma", British Journal of Cancer 2007.
Rosenfeld, et al., "Ranibizumab: Phase III Clinical Trial Results", Ophthalmology clinics of North America 2006.
Sanford, et al., "Reversible phosphorylation differentially affects nuclear and cytoplasmic functions of splicing factor Palternative splicing factor", Proceedings of the National Academy of Sciences of the USA 2005.
Schmidt-Erfurth, et al., "Efficacy and Safety of Monthly versus Quarterly Ranibizumab Treatment in Neovascular Age-related Macular Degeneration: The Excite Study", Ophthalmology 2011.
Spilsbury, et al., "Overexpression of Vascular Endothelial Growth Factor (VEGF) in the Retinal Pigment Epithelium Leads to the Development of Choroidal Neovascularization", American Journal of Pathology 2000.
Varey, et al., "VEGF165b, an antiangiogenic VEGF-A isoform, binds and inhibits bevacizumab treatment in experimental colorectal carcinoma: balance of pro- and antiangiogenic VEGF-A isoforms has implications for therapy", British Journal of Cancer 2008.
Ved, et al., "Anti-angiogenic therapy in treating outer barrier dysfunction in diabetic retinopathy", 2016, Department of Genetics Institute of Ophthalmology UCL.
Ved, et al., "Vascular endothelial growth factor-A165b ameliorates outer-retinal barrier and vascular dysfunction in the diabetic retina", Clinical Science 2017.
Wooland, et al., "VEGF165b, an Inhibitory Vascular Endothelial Growth Factor Splice Variant: Mechanism of Action, In vivo Effect on Angiogenesis and Endogenous Protein Expression", Cancer Research 2004.

* cited by examiner

1-METHYL-1H-PYRAZOL-3-YL
DERIVATIVES FOR USE IN THE
TREATMENT OF NEOVASCULAR DISEASES

CROSS REFERENCE TO RELATED
APPLICATION

This application is a continuation-in-part application of PCT Application No. PCT/GB2021/051810 having an international filing date of Jul. 14, 2021, which designated the United States, which PCT application claimed the benefit of Great Britain Application Serial No. 2010829.6, filed Jul. 14, 2020, both of which are incorporated by reference in their entirety. #

FIELD OF THE INVENTION

The present invention relates to anti-angiogenic treatments and compounds for use in anti-angiogenic treatments, particularly of conditions associated with abnormal angiogenesis or abnormal over-production of pro-angiogenic $VEGF_{xxx}$ isoforms in or on the eye, for example, ocular neovascularization, choroidal neovascularization, age-related macular degeneration and diabetic retinopathy.

The present invention also relates to treatments of hyperpermeability disorders and compounds for use in treating hyperpermeability disorders in the eye, for example diabetic macular oedema.

The present invention also relates to methods of treating or preventing ocular degeneration, for example geographic atrophy or glaucoma, and compounds for use in such methods.

BACKGROUND TO THE INVENTION

Diabetic Macular oedema (DMO, also known as DME) and age-related macular degeneration (AMD), are diseases causing vision loss that affects the central area of the macula, and are the leading cause of blindness in high income countries (Bressler, 2004). DMO results from breakdown of the inner and outer blood retinal barriers as a consequence of increased expression of the pro-angiogenic isoforms of Vascular Endothelial Growth Factor (Perrin et al 2005). This results in both growth of new vessels and leakage of fluid and protein from the vasculature into the retina and increased fluid transport across the retinal pigmented epithelial cells into the retina resulting in retinal oedema and vision loss. Exudative AMD (also known as wet-AMD, or wAMD) is the most severe form of AMD (Ferris et al., 1984) primarily arising from the choroidal circulation beneath the macula and characterized by choroidal neovascularization (CNV). CNV, the abnormal growth of new vessels from the choroid into the retinal pigmented epithelium (RPE) (Patz et al., 1977), is thought to lead to visual loss due to the leakage of blood and serous fluid beneath and through the RPE that eventually leads to loss of photoreceptors, retinal detachment and dense macular scarring (Fine et al., 2000; Campochiaro et al., 2006). Vascular endothelial growth factor (VEGF), a key factor in angiogenesis and vascular leakage (Dvorak et al., 1995) is up-regulated during the progression of DMO and CNV (Spilsbury et al., 2000; Anderson et al., 2002; Das et al., 2003) and has become the lead therapeutic target for the treatment of exudative-AMD.

VEGF is a complex gene that is alternatively spliced to form a family of multiple isoforms (Leung et al., 1989; Jingjing et al., 1999), each isoform differing in biological property, activity and function (Houck et al., 1991). Most cells commonly express isoforms $VEGF_{121}$, $VEGF_{165}$, and $VEGF_{189}$, whereas $VEGF_{145}$ and $VEGF_{206}$ are comparatively rare. The majority of VEGF isoforms contain exons 1-5 (the exception being $VEGF_{111}$ (Mineur et al., 2007)) but differing portions of exons 6 and 7 that encode heparin sulfate (HS) binding domains.

In 2002 differential splicing of the eighth exon was demonstrated from a proximal splice site (PSS) to a distal splice site (DSS) 66 bases downstream (Bates et al., 2002; Woolard et al., 2004). Alternative splicing in this region generated a second family of isoforms ($VEGF_{xxx}b$), noted for their anti-angiogenic (Perrin et al., 2005) and anti-permeability properties. WO 03/012105, the contents of which are incorporated herein by reference in its entirety describes the alternatively spliced isoforms, and their therapeutic significance.

During pathological blood vessel growth, pro-angiogenic, pro-permeability isoforms are selectively upregulated (Bates et al., 2002; Perrin 2005, Varey et al., 2008; Pritchard-Jones et al., 2007), suggesting $VEGF_{xxx}$ and $VEGF_{xxx}b$ may have separate regulatory pathways. These anti-angiogenic isoforms, such as $VEGF_{165}b$ and $VEGF_{121}b$ have been shown to be potently anti-angiogenic, and inhibit VEGF mediated vascular permeability in animal models of retinal and choroidal neovascularisation, following intra-ocular injection (Hua et al 2008, Ved et al 2016), and result in both endothelial, retinal epithelial cell and retinal neuronal cytoprotection (Beazley Long 2015, Magnussen et al 2010). Switching splicing from pro-angiogenic, pro-permeability isoforms to anti-angiogenic, anti-permeability, cyto and neuroprotective isoforms would be a potential therapeutic approach for patients with ocular diseases where vessel leakage, vessel growth, or neuro or epithelial cell degeneration are key contributors to the pathology.

The first therapy to be FDA approved for the treatment of neovascular AMD in December 2004 was a $VEGF_{165}$, $VEGF_{189}$ and $VEGF_{206}$ specific aptamer, Pegaptanib Sodium (Macugen®). During clinical trials pegaptinib dose-dependently reduced the risk of severe visual acuity loss and slowed the progression of neovascular AMD, but did not result in significant improvement in vision. In 2006 Ranibizumab (Lucentis®), a novel humanized anti-VEGF antibody fragment, was FDA approved for the treatment of neovascular AMD. Its approval was based on the results of three clinical trials where, approximately 95% of patients treated monthly with Lucentis® (0.5 mg) maintained visual acuity (defined as the loss of <15 letters) and ≤40% improved vision (defined as the gain of ≥15 letters) at one year compared with 11% in the sham control treated group (Rosenfeld et al., 2006; Brown el al., 2006; Brown et al., 2009). Current treatment regimens require Lucentis administration by intra-ocular injection as often as monthly (Brown et al, 2009; Schmidt-Erfuth et al, 2011). Such intraocular injections result in increased intraocular pressure (Good et al., 2010) and a risk, albeit minor, of endopthalmitis and other severe adverse effects (Jager et al, 2004). Furthermore, bevicizumab (Avastin®), an anti-VEGF antibody from which Lucentis® was derived, was shown to bind $VEGF_{165}b$ with equal potency to $VEGF_{165}$, thus targeting both pro and anti-angiogenic VEGF isoforms (Varey et al 2008), All these treatments require regular injection of agents into the vitreous of people with the disease. This invasive, unpleasant and potentially damaging procedure is required because it has not yet been possible to develop anti-angiogenic agents that target VEGF that are able to penetrate to the RPE and other retinal tissues without injection. The development of topical treatments that would result from solving the problem of how to get molecules to the hack of the eye would be a significant novel approach that would provide a substantial benefit for patients with these and other retinal or ocular neovascular/hyperpermeability diseases.

As both the anti-angiogenic and angiogenic isoforms of VEGF are derived from the same gene, the control of isoform family is a result of the control of alternative splicing. We identified some of the pathways that control the splicing of VEGF at the proximal splice site, implicating the RNA binding protein SRSF1 (Nowak et al., 2008; Amin et al., 2011) and its kinase SRPK1 (Sanford et al., 2005) as key requirements for the decision by cells to use the proximal splice site, and hence generate pro-angiogenic isoforms of VEGF (Nowak et al., 2008; Nowak et al., 2010). Knockdown of SRPK1 potently reduced VEGF mediated angiogenesis in vivo in tumours and inhibition of SRPK1 reduced angiogenesis in vivo (Amin et al., 2011).

WO 2008/110777, WO 2009/106855, WO 2010/058227, WO 2011/148200, and WO 2019/064512, the disclosures of which are incorporated herein by reference, describe therapeutic and other physiological uses of agents which direct expression in favour of the $VEGF_{xxx}b$ isoforms. SRPK inhibitors can in principle constitute such agents.

WO 2005/063293 describes a class of SRPK inhibitors including SRPIN340 and derivatives and analogues thereof.

WO 2014/060763 describes SRPK inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

The development of agents for directing expression of $VEGF_{xxx}b$ isoforms represents a new era not only in the treatment of, for example, neovascular AMD, but all other diseases in which $VEGF_{xxx}b$ is implicated. However, to achieve this, molecules would need to be developed that were both potent SRPK1 inhibitors and permeable through the eye.

The present invention is based on our findings that new small molecule inhibitors have surprisingly and unexpectedly high permeability into the eye as topical treatments, while maintaining SRPK1 inhibitory activity, specifically for use as topical anti-angiogenic agents, neuroprotective agents, agents for use in treating or preventing hyperpermeability disorders, and as agents for treating or preventing ocular fibrosis. The present invention is also based at least in part on the surprising finding that these low molecular weight compounds could be used topically to inhibit CNV progression and angiogenic (but not anti-angiogenic) VEGF expression.

SUMMARY OF THE INVENTION

In a first aspect the invention provides a compound of Formula (I):

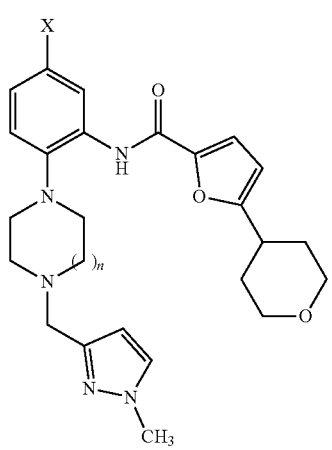

(I)

or a pharmaceutically acceptable salt, solvate, hydrate or prodrug thereof, wherein;

$X=CF_3$, methyl, Cl or cyclopropyl; and n=1 or 2.

The invention also provides a compound of formula (I) for use in the treatment or prevention of ocular neovascularization.

The compounds of formula (I) and their pharmaceutically acceptable salts, solvates, hydrates or prodrugs are new as compounds per se (as well as their use in the prevention and treatments described herein) and they constitute an aspect of the invention.

It is surprising and not expected that the compounds used in the present invention have permeability through the whole eye that enables effective treatment or prevention of ocular neovascularisation or topical treatment or prevention of ocular neovascularization in eyes from animals with similar properties to human eyes in terms of size, thickness, content and function.

Pharmaceutical compositions comprising the novel compounds and the use of the novel compounds and pharmaceutical compositions comprising them in anti-permeability and/or anti-angiogenic treatments (including the treatment and prevention of disorders and diseases characterised by abnormal or excessive ocular angiogenesis or permeability), treatments of ocular hyperpermeability disorders, treatments of ocular neuropathic and neurodegenerative disorders, treatment of ocular epithelial degenerative disorders constitute further aspects of the present invention.

Thus, the present invention also provides (i) methods of treating or preventing disorders and diseases characterized by abnormal or excessive ocular angiogenesis as defined herein; (ii) methods of treating or preventing ocular hyperpermeability disorders as defined herein; (iii) methods of treating or preventing ocular neurodegenerative disorders as defined herein; (iv) and methods of treating or preventing ocular epithelial degenerative disorders; comprising administering a compound of Formula (I) to a patient in need thereof. In some embodiments, for any of the methods described herein, the compound of Formula (I) is administered at a therapeutically effective amount to the patient in need thereof.

The specific compounds of formula (I) and preferred exemplified subclasses of compounds of formula (I) may be particularly mentioned for use in the present invention.

Examples of the compound of formula (I) that may be mentioned include those in which:

n=1, and X is $CF_3$, or Cl; and n=2, and X is $CF_3$, or Cl.

DETAILED DESCRIPTION OF THE INVENTION

The compounds of the present invention are SRPK1-specific inhibitors and may therefore be used in methods of treating or preventing any disease or condition of the eye in which SRPK1 is implicated. Such conditions and treatments will now be described.

Anti-Angiogenic Treatment

The compounds of the present invention may be used in anti-angiogenic treatments in the eye. The anti-angiogenic treatment preferably includes the treatment or prevention of any disease or disorder associated with abnormal angiogenesis or abnormal over-production of pro-angiogenic VEGF isoforms ($VEGF_{xxx}$). Such diseases and disorders include, for example, diabetic retinopathy, trachoma, retrolental hyperplasia, neovascular glaucoma, age-related macular degeneration, haemangioma, corneal angiogenesis associated with ocular injury or infection, and proliferative diabetic retinopathy. The anti-angiogenic treatment according to the present invention may also include non-therapeutic treatments performed on healthy subjects, for example to inhibit vascular development for cosmetic purposes. For further details on diseases and disorders associated with abnormal angiogenesis, and on anti-angiogenic treatments, see WO 2008/110777, the contents of which are incorporated herein by reference.

In particular, the compounds of the present invention may be used in the treatment or prevention of ocular neovascularisation, which may include, but not limited to, retinal neovascularisation or choroidal neovascularisation, diabetic retinopathy or age-related macular degeneration. In addition, the compounds of the present invention may be used in the treatment or prevention of malignant ocular neoplasias or cancers, for example uveal melanoma.

Microvascular Hyperpermeability Disorders, Disorders of Epithelial Cell Survival The compounds of the present invention, as SRPK1 inhibitors, may also be used as therapeutic agents in treating other disorders in which the alternatively spliced $VEGF_{xxx}b$ isoform has been implicated. For example, it has been shown in WO 2010/058227, the contents of which are incorporated herein by reference, that $VEGF_{xxx}b$ is active against a range of microvascular hyperpermeability disorders, disorders of epithelial cell survival and disorders of fenestrations of epithelial filtration membranes.

Microvascular hyperpermeability, disorders of regulation of the pro-angiogenic pro-permeability properties of $VEGF_{xxx}$ isoforms, disorders of epithelial cell survival and permeability, and/or disorders in the nature (for example the number density and/or size) of fenestrations of epithelial filtration membranes underlie a number of serious ocular medical conditions.

Examples of such conditions include, for example, diabetic retinopathy, both proliferative and non-proliferative, diabetic macular oedema, exudative age related macular degeneration and retinal vein occlusion (central and branch).

Examples of disorders where treatment to support epithelial cell survival would be effective are as follows:

age related macular degeneration (AMD) (wet or dry), central serous retinopathy, cystoid macular edema, diabetic retinopathy, proliferative diabetic retinopathy, diabetic macular edema, rubeosis iridis, retinopathy of prematurity, central and branch retinal vein occlusions, inflammatory/infectious retinal neovascularization/edema (e.g., posterior uveitis, sarcoid, toxoplasmosis, histoplasmosis, Vogt-Koyanagi-Harada Disease, chronic uveitis, tuberculososis, syphyllis, punctate and multifocal inner choroidopathy), retinoblastoma, ocular melanoma, ocular tumors, retinal detachment, myopic neovascularization, angiod streaks, Eales disease, ischemic retinopathy (retinal artery occlusion, Takayasu's, carotid artery occlusion), choroidal rupture or any combination thereof. In a most preferred embodiment, the condition at the back of the eye is age related macular degeneration (AMD).

The present invention may be used in the treatment of macular dystrophy. This includes: Stargardt disease/fundus flavimaculatus; Stargardt-like macular dystrophy; Stargardt-like macular dystrophy; Autosomal dominant "bull'seye" macular dystrophy Best macular dystrophy; Adult vitelliform dystrophy; Pattern dystrophy; Doyne honeycomb retinal dystrophy; North Carolina macular dystrophy; Autosomal dominant macular dystrophy resembling MCDR1; North Carolina-like macular dystrophy associated with deafness; Progressive bifocal chorioretinal atrophy; Sorsby's fundus dystrophy; Central areolar choroidal dystrophy; Dominant cystoid macular dystrophy; Juvenile retinoschisis; Occult Macular Dystrophy; Non-familial Occult Macular Dystrophy.

The disorder may particularly be a disorder of the retinal epithelium, such as geographic atrophy, or age related macular degeneration.

For further details on of microvascular hyperpermeability disorders, disorders of epithelial cell survival and disorders of fenestrations of epithelial filtration membranes, and the treatment thereof, see WO 2010/058227, the contents of which are incorporated herein by reference.

Active Compounds

Compounds of the present invention are as defined by Formula (I) and have been shown to be inhibitors of the kinase SRPK1, and thus are useful in treatments of diseases as described herein in which VEGF b and/or SRPK1 have been shown to be implicated. The compounds of the present invention may be SRPK1-specific inhibitors.

The compounds of the present invention may be synthesised by any known method. An exemplary synthesis is described below in the Examples.

Co-Administration

The compounds of the present invention may, if desired, be co-administered with one or more additional active agent, for example one or more agent selected from, but not limited to, cholinesterase inhibitors, dopamine agonists (e.g. L-dopa), COMT inhibitors, MAO-B inhibitors, anti-cholinergics, acetylcholine agonists, serotonin agonists, AMPA receptor agonists, GABA receptor agonists, NMDA receptor agonists, β-adrenoceptor agonists, digoxin, dobutamine, anti-inflammatories, neurotrophic factors, statins, adenosine A2a receptor antagonists, aldose reductase inhibitors, immunomodulators, cannabinoid agonists, interferon or tricyclic anti-depressants.

Definitions

In the definition of formula (I) herein:

"Salt" is not particularly limited, so long as it is a pharmaceutical acceptable salt which is formed with a compound according to the present invention. Such salts include, for example, inorganic acid salts, organic salts, inorganic base salts, organic base salts, and acidic or basic amino acid salts. Examples of preferable inorganic acid salts include: hydrochloride, hydrobromate, sulfate, nitrate, and phosphate. Examples of preferable organic salts include: acetate, succinate, fumarate, maleate, tartrate, citrate, lactate, stearate, benzoate, methanesulfonate, and p-toluene sulfonate.

Examples of preferable inorganic base salts include: alkali metal salts, such as sodium salts and potassium salts; alkali earth metal salts, such as calcium salts and magnesium salts; aluminium salts; and ammonium salts. Examples of preferable organic base salts include: diethylamine salts, diethanol amine salts, meglumine salts, and N,N'-dibenzylethylenediamine salts.

Examples of preferable acidic amino acid salts include: aspartate and glutamate. Examples of preferable basic amino acid salts include: arginine salts, lysine salts, and ornithine salts.

When left in air, the compounds of the present invention sometimes absorb moisture, and are sometimes attached to absorbed water or converted to hydrates. In some embodiments, the hydrate may include hemi-hydrate. Such hydrates are also included in the present invention.

Furthermore, compounds of the present invention are sometimes converted into solvates, absorbing some other solvents. Such solvates are also included in the present invention.

Any organic solvent may in principle be used to prepare a solvate of the compounds of the present invention.

A solvate can include also water together with the one or more organic solvent.

Thus, for example, the solvent may be selected from ketones, alcohols, ethers, esters, aromatic solvents, and, where possible, mixtures thereof with each other, with other organic solvents and/or with water.

Pharmaceutically acceptable prodrug forms of the compounds of Formula (I) may be used in the present invention. "Pharmaceutically acceptable prodrugs" means those prodrugs of the compounds which are, within the scope of sound medical and veterinary judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds. The term "prodrug" means compounds that are rapidly transformed in vivo to yield the parent compound of the above Formula, for example by hydrolysis in blood. Functional groups which may be rapidly transformed, by metabolic cleavage, in vivo form a class of groups reactive with the carboxyl group. Because of the ease with which the metabolically cleavable groups of the compounds are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396,1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgard, 8, p. 1-38, 1992; Journal of Pharmaceutical Sciences, 77, p. 285,1988; Chem. Pharm. Bull., N. Nakeya et al, 32, p. 692,1984; Pro-drugs as Novel Delivery Systems, T. Higuchi and V. Stella, Vol. 14 of the A. C. S. Symposium Series, and Bioreversible Carriers in Drug Design, Edward B. Roche, ed., American Pharmaceutical Association and Pergamon Press, 1987, which are incorporated herein by reference.

Compositions and Administration

The compound according to the present invention may be administered in the form of a composition comprising the active agent and any suitable additional component. The composition may, for example, be a pharmaceutical composition (medicament), suitably for topical administration (e.g. as eyedrops or cream or lotion).

The term "pharmaceutical composition" or "medicament" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of liquid preparations including suspensions, sprays, emulsions, solutions, cachets, granules and liposome preparations. Techniques and formulations generally may be found in Remington, The Science and Practice of Pharmacy, Mack Publishing Co., Easton, PA, latest edition.

Liquid form preparations include solutions, suspensions, and emulsions. As an example may be mentioned water or water-propylene glycol solutions for topical administration. Liquid preparations can also be formulated in solution in aqueous polyethylene glycol solution.

Also included are solid form preparations which are intended to be converted, shortly before use, to liquid form preparations for topical administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof.

The composition may be in a formulation intended for topical application. The formulation may be a gelling formulation to control release and therefore availability of the active agent following topical application. The formulation may contain one or more gelling agents, for example hydroxypropyl methylcellulose. The formulation may contain one or more surfactants, for example a non-ionic liquid polymer, examples of which include Tyloxapol, and the Pluronics® poloxamers from BASF. The formulation may contain one or more solubilizers, for example dextrose or sorbitol. The formulation may contain one or more antimicrobial or antiseptic agents, for example benzalkonium chloride. The aforementioned named gelling agents, surfactants, solubilizers and antimicrobial agents are listed purely by way of example and it will be appreciated that other agents to perform these functions are known.

The dose of the active agent (e.g. a compound of Formula (I)) may be varied depending on the requirements of the patient, the nature, severity and degree of the condition, the age and condition of the patient, the compound being used, and other factors known to those skilled in the art.

In some instances, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired. For example, the total daily dosage may be divided and administered in two, three or four portions during the day. The total daily dosage may be administered in a dosing period ranging from 1 day to 14 days, or longer as required. For example, for long term treatment of chronic eye disorders, the total daily dosage may be administered over a dosing period of at least two years, for example at least three years, for example at least four years, for example at least 5 years, for example at least 10 years, for example at least 15 years, for example at least 20 years.

The dosage regime for administration of the active agent may, for example, comprise a total daily dose of up to 30 mg, for example up to 20 mg, for example up to 10 mg, for example up to 500 µg, for example up to 400 µg, for example up to 300 μg, for example up to 200 μg, for example up to 100 μg, for example up to 50 μg, for example up to 20 μg for example 10 μg of active agent.

The dosage regime for administration of the active agent may, for example, comprise a total daily dose of at least 10 μg, for example at least 20 μg, for example at least 50 μs, for example at least 60 μg, for example at least 100 μg, for example at least 200 μs, for example at least 300 μs, for example at least 400 μg, for example at least 500 μg, for example at least 1 mg, for example at least 10 mg, for example at least 20 mg, for example at least 30 mg of active agent.

The compound of Formula (I) or a pharmaceutically acceptable salt, solvate, hydrate or prodrug thereof may be administered in a therapeutically effective amount. As used herein, the term "therapeutically effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

A therapeutically effective amount of a compound of Formula (I) for topical administration for treatment of CNV may be at least about 5 μg/10 μL of delivery vehicle. Alternatively, a therapeutically effective amount may be at least about 100 μg/mL, for example at least about 200 μg/mL, at least about 300 μg/mL, at least about 400 μg/mL, at least about 500 μg/mL, at least about 600 μg/mL, at least about 700 μg/mL, at least about 800 μg/mL, at least about 900 μg/mL, or at least about 1000 μg/mL. Alternatively, a therapeutically effective amount may be at least about 1 mg/mL, for example at least about 1.5 mg/mL, for example at least about 2 mg/mL, at least about 3 mg/mL, at least about 4 mg/mL, at least about 5 mg/mL. Alternatively, a therapeutically effective amount may be less than about 5 mg/mL, for example less than about 4 mg/mL, less than about 3 mg/mL, less than about 2 mg/mL, less than about 1.5 mg/mL, less than about 1 mg/mL. The therapeutically effective amount may be administered daily, for a dosing period ranging, for example, between 1 and 14 days. The therapeutically effective amount may also be administered daily, for life, for example in the long term treatment of a chronic eye disorder. The therapeutically effective amount may be a total daily dosage which may be divided and administered in portions during the day, for example twice daily or four times daily.

"Treating or Preventing"

The expression "treating or preventing" and analogous terms used herein refers to all forms of healthcare intended to remove or avoid the disorder or to relieve its symptoms, including preventive, curative and palliative care, as judged according to any of the tests available according to the prevailing medical and psychiatric practice. An intervention that aims with reasonable expectation to achieve a particular result but does not always do so is included within the expression "treating or preventing". An intervention that succeeds in slowing or halting progression of a disorder is included within the expression "treating or preventing".

As used herein, unless otherwise noted, the terms "treating", "treatment" and the like, shall include the management and care of a subject or patient, preferably a mammal, more preferably a human, for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder. The terms "treating" or "treatment" further include: (a) inhibiting the disease-state, i.e., arresting its development; and/or (b) relieving the disease-state, i.e., causing regression of the disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a pharmaceutically acceptable salt, hydrate, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

"Susceptible To"

The expression "susceptible to" and analogous terms used herein refers particularly to individuals at a higher than normal risk of developing a medical or psychiatric disorder, or a personality change, as assessed using the known risk factors for the individual or disorder. Such individuals may, for example, be categorised as having a substantial risk of developing one or more particular disorders or personality changes, to the extent that medication would be prescribed and/or special dietary, lifestyle or similar recommendations would be made to that individual.

Mammals

Besides being useful for human treatment, the present invention is also useful in a range of mammals. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs).

Where the disorder or function to be treated is exclusive to humans, then it will be understood that the mammal to be treated is a human. The same applies respectively to any other mammalian species if the disorder or function to be treated is exclusive to that species.

BRIEF DESCRIPTION OF THE DRAWINGS

Embodiments of the present invention will now be described, purely by way of example, and with reference to the accompanying drawings, in which.

METHODS

Synthesis

Figure 1:
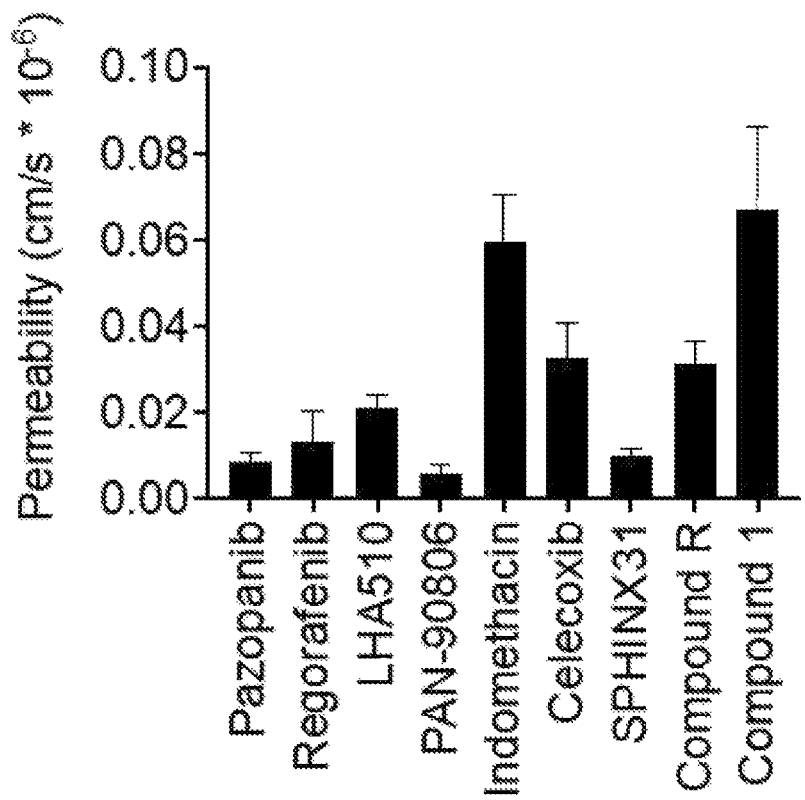
FIG. 1 shows the permeability of compound 1 and other compounds as measured by the methods described under the ocular permeability section.

The compounds of the invention can be prepared by any synthetic method known to the skilled person, for example based on those described in WO2015/159103 and WO2017/064512. Specifically, Compounds 1 to 3 were prepared according to the following exemplary methodologies.

Compound 1 tert-Butyl 4-(2-nitro-4-(trifluoromethyl)phenyl)piperazine-1-carboxylate

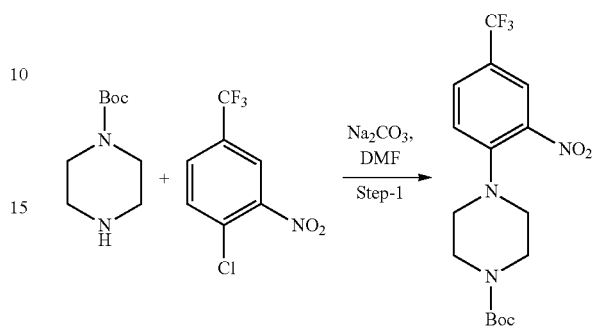

A suspension of tert-butyl piperazine-1-carboxylate (2.90 g, 15.5 mmol), 1-chloro-2-nitro-4-(trifluoromethyl) benzene (3.99 g, 15.5 mmol) and sodium carbonate (4.10 g, 38.66 mmol) in DMF (25 mL) was heated to 110° C. for 3 h. The resulting reaction mixture was allowed to cool to room temperature and quenched with cold water (100 mL) and extracted with ethyl acetate (×3). The organic extracts were combined and washed with brine, then dried over anhydrous $Na_2SO_4$. The solvent was removed under reduced pressure to afford the title product as an orange liquid (5.4 g, 92%), which was of sufficient purity to use in the next step with all analytical data matching the required structure.

$^1$H NMR (400 MHz, DMSO-$d_6$) δ 1.41 (s, 9H), 3.12-3.15 (m, 4H), 3.45 (br s, 4H), 7.45 (d, J=8.8 Hz, 1H), 7.89 (dd, J=2, 9.2 Hz, 1H), 8.18 (d, J=1.6 Hz, 1H); LCMS: [M$^+$−56] 320.01 m/z, 98.37% purity.

tert-Butyl 4-(2-amino-4-(trifluoromethyl)phenyl)piperazine-1-carboxylate

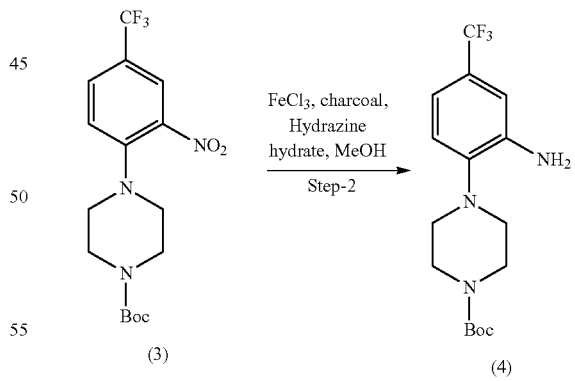

Hydrazine hydrate (17.87 g, 357.5 mmol) was added drop wise to a solution of piperazine (5.4 g, 14.3 mmol), iron(III) chloride (0.46 g, 2.8 mmol) and charcoal (2.7 g) in methanol (50 mL) at 0° C. temperature under nitrogen atmosphere. The resulting reaction mixture was heated to reflux temperature for 1 h. The reaction mixture was allowed to cool to room temperature then filtered through a short pad of Celite, eluting with ethyl acetate. The organic filtrate was concentrated under reduced pressure. The residue was diluted with water (50 mL) and extracted with ethyl acetate (×3). The organic extracts were combined and dried anhydrous Na$_2$SO$_4$. The solvent was removed under reduced pressure. The resulting crude material was triturated by n-pentane (2×10 mL) to afford the title product as an off-white solid (3.5 g, 71%).

$^1$H NMR (400 MHz, DMSO-d$_6$) δ 1.42 (s, 9H), 2.76-2.78 (m, 4H), 3.50 (br s, 4H), 5.23 (br s, 2H), 6.82 (dd, J=1.6, 8 Hz, 1H), 6.96-7.01 (m, 2H); LCMS: [M$^+$−56] 290.01 m/z, 98.80% purity.

N-(2-(piperazin-1-yl)-5-(trifluoromethyl)phenyl)-5-(tetrahydro-2H-pyran-4-yl)furan-2-carboxamide

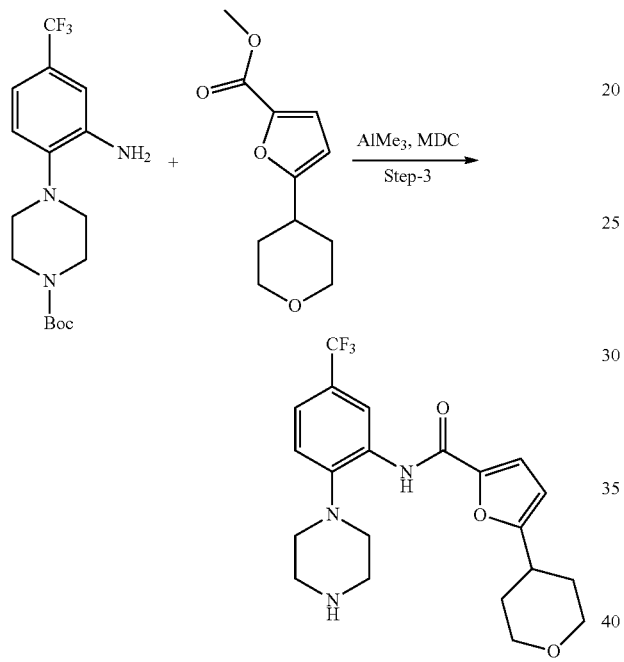

A 2 M solution of trimethylaluminium in toluene (8.7 mL, 17.37 mmol) was added drop wise to a solution of tert-butyl 4-(2-amino-4-(trifluoromethyl)phenyl)piperazine-1-carboxylate (2 g, 5.8 mmol) in dichloromethane (8 mL) at 0° C. temperature under nitrogen atmosphere. The reaction mixture was stirred at room temperature for 1 h after which, a solution methyl 5-(tetrahydro-2H-pyran-4-yl)-2-furoate (1.22 g, 5.8 mmol) in dichloromethane (5 mL) was added drop wise at room temperature. The resulting reaction solution was stirred at room temperature for an additional 15 h. To quench the reaction saturated aqueous solution of Rochelle's salt was added drop wise at room temperature and the solution was allowed to stir at room temperature for additional 15 min. The reaction mixture was diluted with saturated aqueous sodium bicarbonate solution (100 mL) and extracted with dichloromethane (×3). The organic extracts were combined and washed with water and brine, then dried over anhydrous Na$_2$SO$_4$. The solvent was removed under reduced pressure to afford the title product as a light yellow solid (1.8 g, 73%).

$^1$H-NMR (DMSO-d$_6$) δ 1.65-1.76 (m, 2H), 1.94 (dd, J=2, 12.4 Hz, 2H), 2.85-2.88 (m, 4H), 2.97-2.99 (m, 4H), 3.01-3.09 (m, 1H), 3.45-3.51 (m, 2H), 3.91-3.95 (m, 2H), 6.46 (dd, J=0.8, 3.6 Hz, 1H), 7.26 (d, J=3.2 Hz, 1H), 7.43-7.49 (m, 2H), 8.56 (d, J=2 Hz, 1H), 9.45 (s, 1H). LCMS: [MH]$^+$424.22 m/z, 43.56% purity.

N-(2-(4-((1-methyl-1H-pyrazol-3-yl)methyl)piperazin-1-yl)-5-(trifluoromethyl)phenyl)-5-(tetrahydro-2H-pyran-4-yl)furan-2-carboxamide

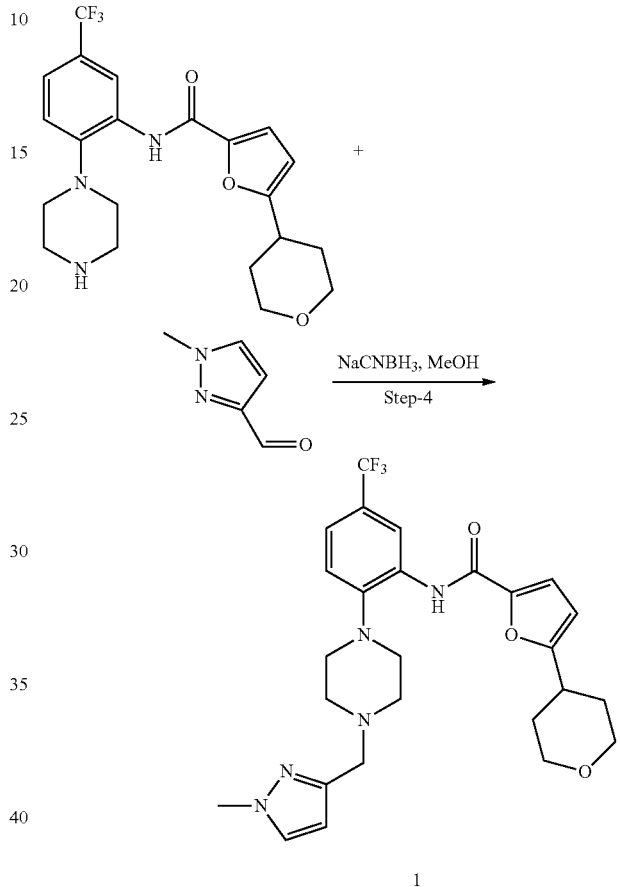

1

A solution of the piperazine (0.10 g, 0.23 mmol), 1-methyl-1H-pyrazole-3-carbaldehyde (0.026 g, 0.23 mmol) in methanol (5 mL) was stirred at ambient temperature for 30 min under nitrogen atmosphere. Then sodium cyanoborohydride (0.44 g, 0.71 mmol) was added portion wise into the reaction mixture at 0° C. The resulting reaction mixture was allowed to stir at room temperature for 2 h. The reaction mixture was then diluted with saturated sodium bicarbonate solution (20 mL) and extracted with ethyl acetate (×3). The organic extracts were combined and washed with brine, then dried over anhydrous Na$_2$SO$_4$. The solvent was removed under reduced pressure. The resulting crude material was purified by preparative HPLC using 10 mM ammonium bicarbonate in water and acetonitrile as mobile phase to afford the title product (Compound 1) as an off white solid (0.05 g, 40.91%).

Mp: 148-150° C.; $^1$H NMR (400 MHz, DMSO-d$_6$) δ 1.71-1.82 (m, 2H), 1.97-2.00 (m, 2H), 2.65-2.67 (m, 4H), 2.92 (br s, 4H), 3.06-3.12 (m, 1H), 3.47-3.54 (m, 4H), 3.78 (s, 3H), 3.98 (d, J=9.6 Hz, 2H), 6.15 (s, 1H), 6.47 (d, J=3.2 Hz, 1H), 7.25 (d, J=3.6 Hz, 1H), 7.47 (s, 2H), 7.62 (s, 1H), 8.61 (s, 1H), 9.47 (s, 1H).

HPLC purity: 100%

MS (ESI-MS): m/z calcd for $C_{26}H_{31}F_3N_5O_3$ [MH]+ 518.24, found 518.12

Compound 2 tert-Butyl 4-(2-nitro-4-(trifluoromethyl)phenyl)-1,4-diazepane-1-carboxylate

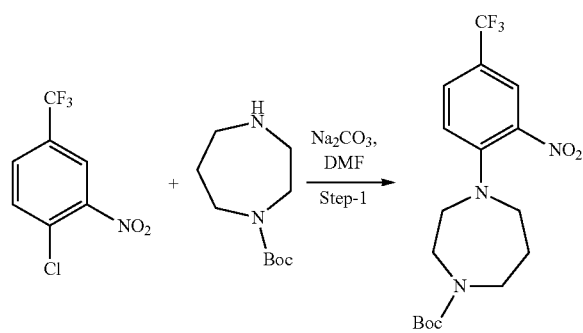 [SMILES: O=[N+]([O-])c1cc(C(F)(F)F)ccc1Cl ; CC(C)(C)OC(=O)N1CCCNCC1 ; CC(C)(C)OC(=O)N1CCCN(c2ccc(C(F)(F)F)cc2[N+](=O)[O-])CC1]

A suspension of 1-chloro-2-nitro-4-(trifluoromethyl)benzene (2.25 g, 9.99 mmol), tert-butyl 1,4-diazepane-1-carboxylate (2.0 g, 9.99 mmol) and solid sodium carbonate (3.18 g, 29.96 mmol) in anhydrous DMF (30 mL) was heated to 110° C. for 17 h. The resulting reaction mixture was allowed to cool to room temperature and the reaction mixture was filtered through a short pad of Celite, eluting with ethyl acetate. The organic filtrate was concentrated under reduced pressure. The residue was diluted with water (100 mL) and extracted with ethyl acetate (×3). The organic extracts were combined and dried over anhydrous $Na_2SO_4$. The solvent was removed under reduced pressure. The resulting crude material was purified by column chromatography on silica using (90% ethyl acetate in hexane) as an eluent to afford the title product as a light yellow solid (3.78 g, 97%).

$^1$H NMR (400 MHz, DMSO-$d_6$) δ 1.12-1.20 (m, 9H), 1.80 (br s, 2H), 3.12-3.24 (m, 2H), 3.30-3.38 (m, 2H, merged in moisture residual of DMSO), 3.50 (t, J=6 Hz, 2H), 3.61-3.69 (m, 2H), 7.35-7.40 (m, 1H), 7.72 (d, J=8.8 Hz, 1H), 8.02-8.03 (m, 1H); LCMS: [M+-56] 334.08 m/z, 100% purity.

1-(2-Nitro-4-(trifluoromethyl)phenyl)-1,4-diazepane

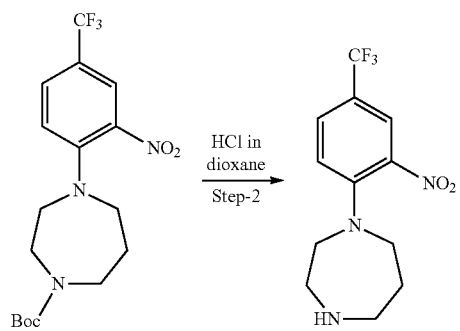 [SMILES: CC(C)(C)OC(=O)N1CCCN(c2ccc(C(F)(F)F)cc2[N+](=O)[O-])CC1 ; O=[N+]([O-])c1cc(C(F)(F)F)ccc1N1CCCNCC1]

4N HCl in dioxane (25 mL) was added drop wise to a solution of tert-butyl 4-(2-nitro-4-(trifluoromethyl)phenyl)-1,4-diazepane-1-carboxylate (3.78 g, 9.71 mmol) in dioxane (10 mL) at 0° C. temperature under nitrogen atmosphere. The resulting reaction mixture was stirred at room temperature for 2 h. After completion of reaction, the reaction mixture was poured into a saturated solution of sodium bicarbonate (100 mL). The product was extracted with ethyl acetate (×3). The organic extracts were combined and washed with water and brine, then dried over anhydrous $Na_2SO_4$. The solvent was removed under reduced pressure to afford the title product as an orange liquid (2.85 g, quantitative), which was used directly in the next step without further purification.

$^1$H NMR (400 MHz, DMSO-$d_6$) δ 1.79-1.81 (m, 2H), 2.78 (t, J=5.2 Hz, 2H), 2.97 (t, J=5.2 Hz, 2H), 3.19 (d, J=4.8 Hz, 2H), 3.46 (t, J=5.2 Hz, 2H), 7.36 (d, J=9.2 Hz, 1H), 7.72 (dd, J=2.4, 9.2 Hz, 1H), 8.04 (d, J=1.6 Hz, 1H); LCMS: [MH]+289.96 m/z, 99.97% purity.

1-((1-Methyl-1H-pyrazol-3-yl)methyl)-4-(2-nitro-4-(trifluoromethyl)phenyl)-1,4-diazepane

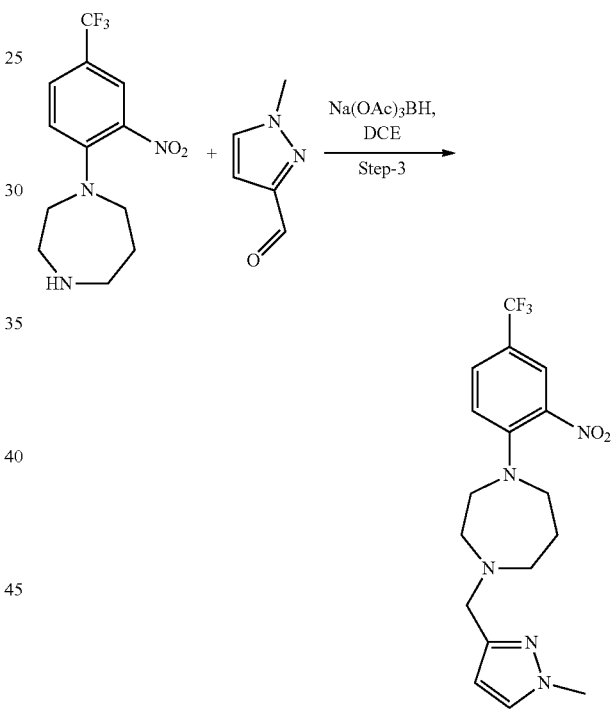

A solution of 1-(2-nitro-4-(trifluoromethyl)phenyl)-1,4-diazepane (1.4 g, 4.84 mmol) and 1-methyl-1H-pyrazole-3-carbaldehyde (5) (0.639 g, 5.81 mmol) in 1,2-dichloroethane (25 mL) was added sodium sulfate (0.343 g, 2.42 mmol) followed by glacial acetic acid (0.581 g, 9.68 mmol). The resulting reaction mixture was stirred at ambient temperature for 3 h under nitrogen atmosphere. Then sodium triacetoxyborohydride (1.54 g, 7.26 mmol) was added portion wise into the reaction mixture at 0° C. temperature. The resulting reaction mixture was allowed to stir at room temperature for 4 h. The reaction mixture was then diluted with saturated sodium bicarbonate solution (100 mL) and extracted with ethyl acetate (×3). The organic extracts were combined and washed with brine, then dried over anhydrous $Na_2SO_4$. The solvent was removed under reduced pressure. The resulting crude material was purified by flash chromatography on silica using (4% methanol in chloroform) as an eluent to afford the title product as an orange liquid (1.80 g, 97%).

¹H NMR (400 MHz, CDCl₃) δ 2.01 (quin, J=5.2 Hz, 2H), 2.74 (t, J=5.2 Hz, 2H), 2.84 (t, J=4.8 Hz, 2H), 3.37 (t, J=5.6 Hz, 2H), 3.47 (t, J=4.4 Hz, 2H), 3.67 (s, 2H), 3.89 (s, 3H), 6.17 (d, J=2 Hz, 1H), 7.01 (d, J=9.2 Hz, 1H), 7.31 (d, J=2 Hz, 1H), 7.56 (dd, J=2, 8.8 Hz, 1H), 8.03 (d, J=1.2 Hz, 1H); LCMS: [W]⁺384.14 m/z, 99.35% purity.

2-(4-((1-Methyl-1H-pyrazol-3-yl)methyl)-1,4-diazepan-1-yl)-5-(trifluoromethyl)aniline

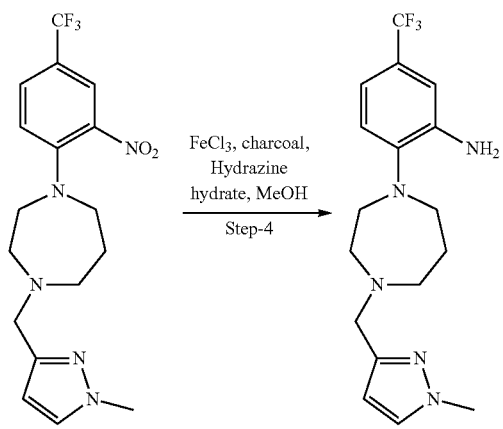 [SMILES: Cn1ccc(CN2CCCN(c3ccc(C(F)(F)F)cc3[N+](=O)[O-])CC2)n1 ; Cn1ccc(CN2CCCN(c3ccc(C(F)(F)F)cc3N)CC2)n1]

Hydrazine hydrate (5.88 g, 117.38 mmol) was added drop wise to a solution of 1-((1-methyl-1H-pyrazol-3-yl)methyl)-4-(2-nitro-4-(trifluoromethyl)phenyl)-1,4-diazepane (1.80 g, 4.70 mmol), iron(III) chloride (0.125 g, 0.94 mmol) and charcoal (0.2 g) in methanol (30 mL) at 0° C. temperature under nitrogen atmosphere. The resulting reaction mixture was heated to reflux temperature for 30 min. The reaction mixture was allowed to cool to room temperature then filtered through a short pad of Celite, eluting with ethyl acetate. The organic filtrate was concentrated under reduced pressure. The residue was diluted with water (50 mL) and extracted with ethyl acetate (×3). The organic extracts were combined and dried over anhydrous Na₂SO₄. The solvent was removed under reduced pressure. The resulting crude material was purified by flash chromatography on silica using (4% methanol in chloroform) as an eluent to afford the title product as a colorless liquid (1.4 g, 84%).

¹H NMR (400 MHz, DMSO-d₆) δ 1.81 (quin, J=5.6 Hz, 2H), 2.71-2.75 (m, 4H), 3.01-3.07 (m, 4H), 3.58 (s, 2H), 3.77 (s, 3H), 5.07 (br s, 2H), 6.14 (d, J=2 Hz, 1H), 6.80 (dd, J=1.6, 8 Hz, 1H), 6.93 (d, J=2 Hz, 1H), 7.04 (d, J=8 Hz, 1H), 7.58 (d, J=2 Hz, 1H); LCMS: [MH]⁺354.22 m/z, 100% purity.

N-(2-(4-((1-methyl-1H-pyrazol-3-yl)methyl)-1,4-diazepan-1-yl)-5-(trifluoromethyl)phenyl)-5-(tetrahydro-2H-pyran-4-yl)furan-2-carboxamide

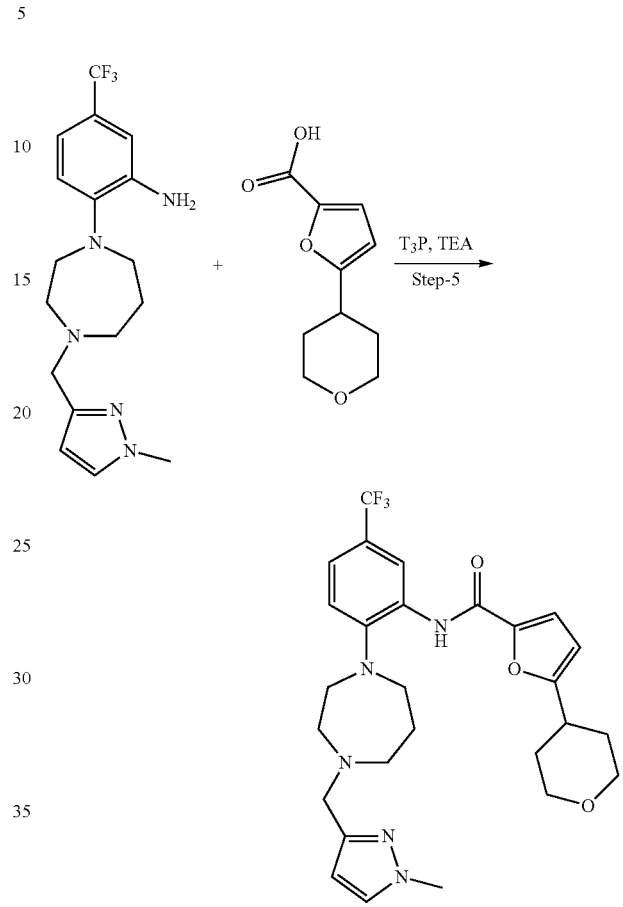

To a solution of 2-(4-((1-methyl-1H-pyrazol-3-yl)methyl)-1,4-diazepan-1-yl)-5-(trifluoromethyl)aniline (0.2 g, 0.56 mmol) and 5-(tetrahydro-2H-pyran-4-yl)-2-furoic acid (0.133 g, 0.67 mmol) in tetrahydrofuran (8 mL) were added triethylamine (0.114 g, 1.13 mmol) and T₃P (0.179 g, 0.56 mmol) at room temperature under nitrogen atmosphere. The resulting reaction mixture was heated to reflux temperature for 4 h. The reaction mixture was allowed to cool to room temperature and diluted with water (100 mL) and extracted with ethyl acetate (×3). The organic extracts were combined and dried over anhydrous Na₂SO₄. The organic solvent was removed under reduced pressure. The resulting crude material was purified by preparative HPLC using Isopropyl alcohol: methanol (70:30) and n-heptane as mobile phase to afford the title product (Compound 2) as a brown semi-solid (0.059 g, 19.61%).

¹H NMR (400 MHz, DMSO-d₆) δ 1.64-1.74 (m, 2H), 1.90-1.93 (m, 4H), 2.77-2.79 (m, 4H), 2.98-3.04 (m, 1H), 3.13-3.16 (m, 4H), 3.42-3.47 (m, 2H), 3.58 (s, 2H), 3.77 (s, 3H), 3.91 (d, J=9.6 Hz, 2H), 6.13 (d, J=2 Hz, 1H), 6.43 (d, J=3.2 Hz, 1H), 7.24 (d, J=3.6 Hz, 1H), 7.38-7.46 (m, 2H), 7.59 (d, J=1.6 Hz, 1H), 8.35 (s, 1H), 9.55 (s, 1H).

HPLC purity: 100%

MS (ESI-MS): m/z calcd for C₂₇H₃₃F₃N₅O₃ [MH]⁺ 532.25, found 532.08

Compound 3 tert-Butyl 4-(4-chloro-2-nitrophenyl)-1,4-diazepane-1-carboxylate

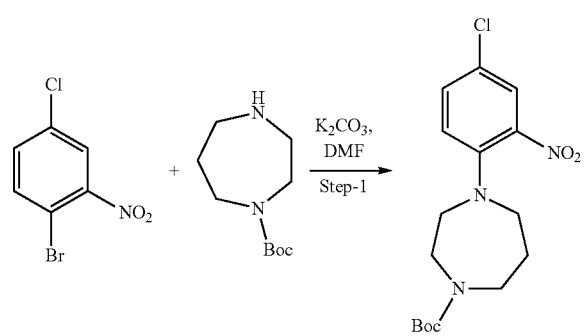 [SMILES: O=[N+]([O-])c1cc(Cl)ccc1Br ; CC(C)(C)OC(=O)N1CCCNCC1 ; CC(C)(C)OC(=O)N1CCCN(c2ccc(Cl)cc2[N+](=O)[O-])CC1]

A suspension of 1-bromo-4-chloro-2-nitrobenzene (2.36 g, 9.98 mmol), tert-butyl 1,4-diazepane-1-carboxylate (2.0 g, 9.98 mmol) and solid sodium carbonate (4.14 g, 29.94 mmol) in anhydrous DMF (30 mL) was heated to 110° C. for 17 h. The resulting reaction mixture was allowed to cool to room temperature and the reaction mixture was filtered through a short pad of Celite, eluting with ethyl acetate. The organic filtrate was concentrated under reduced pressure. The residue was diluted with water (100 mL) and extracted with ethyl acetate (×3). The organic extracts were combined and dried over anhydrous $Na_2SO_4$. The solvent was removed under reduced pressure. The resulting crude material was purified by column chromatography on silica using (100% chloroform) as an eluent to afford the title product as an orange liquid (3.20 g, 57%).

$^1$H NMR (400 MHz, $CDCl_3$) δ 1.39-1.48 (m, 9H), 1.95 (br s, 2H), 3.21-3.43 (m, 4H), 3.51-3.57 (m, 4H), 7.10 (d, J=8.8 Hz, 1H), 7.37 (dd, J=2.8, 9.2 Hz, 1H), 7.69 (d, J=2.8 Hz, 1H); LCMS: [M$^+$–56] 299.87 m/z, 100% purity.

1-(4-Chloro-2-nitrophenyl)-1,4-diazepane

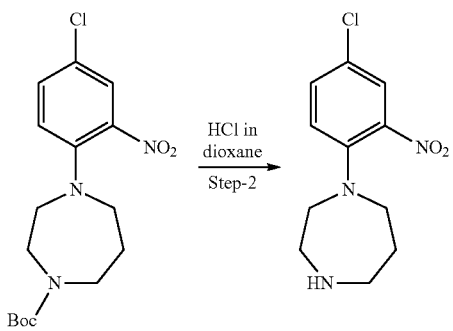 [SMILES: CC(C)(C)OC(=O)N1CCCN(c2ccc(Cl)cc2[N+](=O)[O-])CC1 ; O=[N+]([O-])c1cc(Cl)ccc1N1CCCNCC1]

4N HCl in dioxane (20 mL) was added drop wise to a solution of tert-butyl 4-(4-chloro-2-nitrophenyl)-1,4-diazepane-1-carboxylate (2.20 g, 6.18 mmol) in dioxane (10 mL) at 0° C. temperature under nitrogen atmosphere. The resulting reaction mixture was stirred at room temperature for 15 h. After completion of reaction, the reaction mixture was poured into a saturated solution of sodium bicarbonate (100 mL) and extracted with ethyl acetate (×3). The organic extracts were combined and washed with water and brine, then dried over anhydrous $Na_2SO_4$. The solvent was removed under reduced pressure to afford the title product as a yellow solid (1.7 g, quantitative), which was used directly in the next step without further purification.

$^1$H NMR (400 MHz, DMSO-$d_6$) δ 2.73 (t, J=5.2 Hz, 2H), 2.88 (t, J=4.8 Hz, 2H), 3.10 (t, J=4.8 Hz, 2H), 3.36 (t, J=5.6 Hz, 2H), 7.23 (d, J=9.6 Hz, 1H), 7.49 (dd, J=2.8, 9.2 Hz, 1H), 7.79 (d, J=2.8 Hz, 1H); LCMS: [MH]$^+$255.96 m/z, 100% purity.

1-(4-Chloro-2-nitrophenyl)-4-((1-methyl-1H-pyrazol-3-yl)methyl)-1,4-diazepane

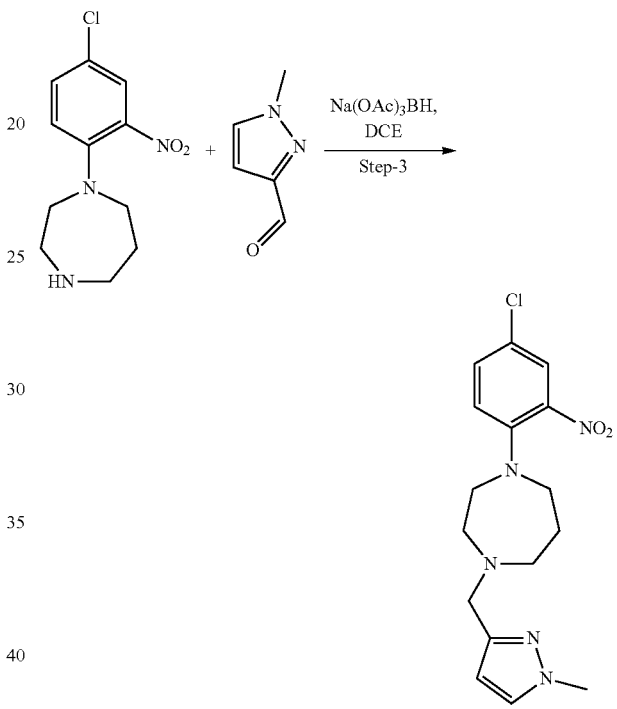

A solution of 1-(4-chloro-2-nitrophenyl)-1,4-diazepane (0.5 g, 1.96 mmol) and 1-methyl-1H-pyrazole-3-carbaldehyde (0.258 g, 2.35 mmol) in 1,2-dichloroethane (12 mL) was added sodium sulfate (0.138 g, 0.97 mmol) followed by glacial acetic acid (0.234 g, 3.91 mmol) at rt. The resulting reaction mixture was stirred at ambient temperature for 6 h under nitrogen atmosphere. Then sodium triacetoxyborohydride (0.621 g, 2.93 mmol) was added portion wise into the reaction mixture at 0° C. temperature. The resulting reaction mixture was allowed to stir at room temperature for 17 h. The reaction mixture was then diluted with saturated sodium bicarbonate solution (100 mL) and extracted with ethyl acetate (×3). The organic extracts were combined and washed with brine, then dried over anhydrous $Na_2SO_4$. The solvent was removed under reduced pressure. The resulting crude material was purified by flash chromatography on silica using (2% methanol in chloroform) as an eluent to afford the title product as an orange liquid (0.78 g, quantitative).

$^1$H NMR (400 MHz, $CDCl_3$) δ 1.70 (br s, 2H), 3.10 (br s, 4H), 3.27-3.30 (m, 4H), 3.92 (s, 3H), 3.97 (br s, 2H), 6.46 (br s, 1H), 7.09 (d, J=9.2 Hz, 1H), 7.38-7.45 (m, 2H), 7.70-7.72 (m, 1H); LCMS: [MH]$^+$350.03 m/z, 98.32% purity.

5-Chloro-2-(4-(O-methyl-1H-pyrazol-3-yl)methyl)-1,4-diazepan-1-yl)aniline

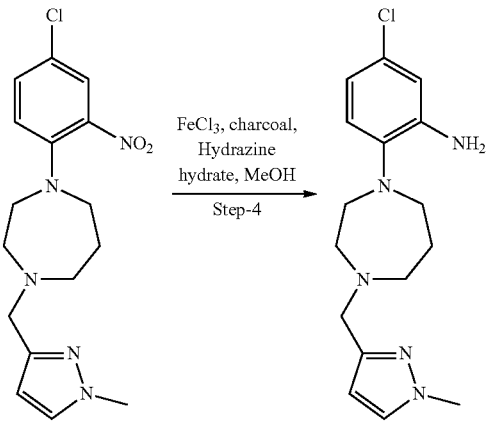 [SMILES: Cn1ccc(CN2CCCN(c3ccc(Cl)cc3[N+](=O)[O-])CC2)n1 ; Cn1ccc(CN2CCCN(c3ccc(Cl)cc3N)CC2)n1]

Hydrazine hydrate (2.79 g, 55.74 mmol) was added drop wise to a solution of 1-(4-chloro-2-nitrophenyl)-4-((1-methyl-1H-pyrazol-3-yl)methyl)-1,4-diazepane (0.78 g, 2.23 mmol), iron(III) chloride (0.072 g, 0.44 mmol) and charcoal (0.1 g) in methanol (30 mL) at 0° C. temperature under nitrogen atmosphere. The resulting reaction mixture was heated to reflux temperature for 30 min. The reaction mixture was allowed to cool to room temperature then filtered through a short pad of Celite, eluting with ethyl acetate. The organic filtrate was concentrated under reduced pressure. The residue was diluted with water (50 mL) and extracted with ethyl acetate (×3). The organic extracts were combined and dried over anhydrous $Na_2SO_4$. The solvent was removed under reduced pressure. The resulting crude material was purified by flash chromatography on silica using (2% methanol in chloroform) as an eluent to afford the title product as a light brown liquid (0.5 g, 70%).

$^1$H NMR (400 MHz, DMSO-$d_6$) δ 1.82 (br s, 2H), 2.78 (br s, 4H), 2.96 (t, J=5.6 Hz, 4H), 3.64 (br s, 2H), 3.78 (s, 3H), 5.03 (br s, 2H), 6.18 (br s, 1H), 6.48 (d, J=2.4, 8.4 Hz, 1H), 6.65 (d, J=2.4 Hz, 1H), 6.90 (d, J=8.4 Hz, 1H), 7.61 (br s, 1H); LCMS: [MH]$^+$320.07 m/z, 100% purity.

N-(5-chloro-2-(4-((1-methyl-1H-pyrazol-3-yl)methyl)-1,4-diazepan-1-yl)phenyl)-5-(tetrahydro-2H-pyran-4-yl)furan-2-carboxamide

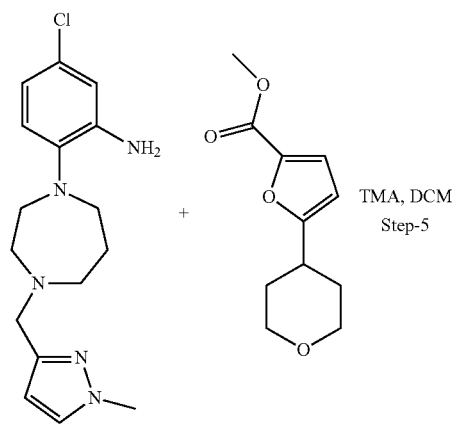

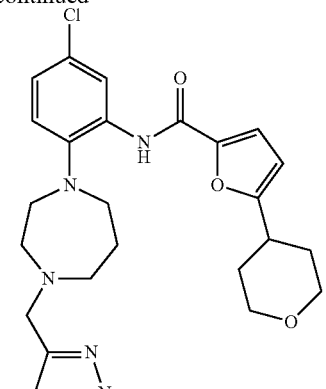

A 2.0 M solution of trimethylaluminium in toluene (0.93 mL, 1.88 mmol) was added drop wise to a solution of 5-chloro-2-(4-((1-methyl-1H-pyrazol-3-yl)methyl)-1,4-diazepan-1-yl)aniline (0.2 g, 0.62 mmol) in dichloromethane (8 mL) at 0° C. temperature under nitrogen atmosphere. The mixture was stirred at room temperature for 1 h after which, a solution of methyl 5-(tetrahydro-2H-pyran-4-yl)-2-furoate (0.131 g, 0.62 mmol) in dichloromethane (3 mL) was added drop wise at room temperature under nitrogen atmosphere. The resulting reaction mixture was stirred at room temperature for 21 h. The resulting reaction mixture was diluted with saturated aqueous sodium bicarbonate solution (50 mL) and extracted with dichloromethane (×3). The organic extracts were combined, brine washed and dried over anhydrous $Na_2SO_4$. The solvent was removed under reduced pressure. The resulting crude material was purified by preparative HPLC using 0.1% formic acid in water and acetonitrile as a mobile phase to afford the title product (Compound 3) as a brown solid (0.035 g, 11.24%).

Mp: 148-150° C.; $^1$H NMR (400 MHz, DMSO-$d_6$) δ 1.67-1.71 (m, 2H), 1.87-1.93 (m, 4H), 2.76 (br s, 2H), 2.83 (t, J=5.6 Hz, 2H), 3.01-3.04 (m, 5H), 3.44 (td, J=8, 11.6 Hz, 2H), 3.60 (br s, 2H), 3.77 (s, 3H), 3.91 (dd, J=2, 11.6 Hz, 2H), 6.14 (d, J=2 Hz, 1H), 6.44 (dd, J=0.8, 3.6 Hz, 1H), 7.13 (dd, J=2.8, 8.4 Hz, 1H), 7.23 (d, J=3.6 Hz, 1H), 7.33 (d, J=8.8 Hz, 1H), 7.60 (d, J=2 Hz, 1H), 8.29 (d, J=2.4 Hz, 1H), 9.61 (s, 1H).

HPLC purity: 98.70%

MS (ESI-MS): m/z calcd for $C_{26}H_{33}ClN_5O_3$ [W]$^+$498.23, found 498.12

In Vitro Kinase Assay

Kinase assays were carried out by the MRC Dundee Kinase Centre using a radioactive filter binding assay using $^{33}$P ATP (Hastie, et al 2006. Nat Protoc. 2006; 1(2):968-71; Bain, et al 2007. Biochem J. 2007 Dec. 15; 408(3):297-315).

In vivo angiogenesis assay: Laser-induced choroidal neovascularisation (CNV) protocol 6-8 week-old female C57/B6 mice were anesthetized with an intraperitoneal injection of a mixture of 50 mg/kg ketamine and 0.5 mg/kg medetomidine. The pupils were immediately dilated by topical (eyedrop) application with a dilator such as 5% phenylephrine hydrochloride and 1% tropicamide. Four photocoagulation lesions were delivered with a green Merilas 532α laser (450 mW, 130 ms) between the "large" retinal vessels in clear space with no vessels in a peripapillary distribution at a distance of 1-2 disc-diameters in each eye. Only clean laser lesions with a subretinal bubble at the time of treatment were included in the study. Immediately following laser photocoagulation the animals were given topical eye drops of candidate compounds twice daily at 2 µg/mL, 0.2 µg/mL or 0.066 µg/mL or eye drop formulation control as indicated (10 µL, eyes held for 30 seconds to prevent animal wiping drop away). Experiments were performed with an initial eye drop formulation containing 1% hydroxypropyl methyl cellulose, 0.2% tyloxapol, 3.4% dextrose, 0.006% benzalkonium chloride, and 0.025% ethylenediaminetetraacetic acid with 1% DMSO in PBS and data were confirmed in a second eye drop formulation containing 7% poly-oxyl-40-stearate and 4% dextrose in PBS.

After one week, mice were anesthetized with an intraperitoneal injection of a mixture of 50 mg/kg ketamine and 0.5 mg/kg medetomidine. The pupils were immediately dilated by topical (eyedrop) application with a dilator such as 5% phenylephrine hydrochloride and 1% tropicamide. Mice were administered an intraperitoneal injection of sodium fluorescein (10%). Phase contrast and green fluorescent fundus images were taken with an angiography microscope and camera with each lesion in focus. The mice were killed by a schedule 1 method and eyes were either unfixed for retinal dissection and protein extraction, or fixed and enucleated and choroids stained and examined.

VEGF ELISA with $VEGF_{165}a$ Capture Antibodies 96-well clear microplate (high sensitivity thermo immulon or costar 9018) were coated with 100 µL of 10 µg/mL $VEGF_{xxx}b$ or 0.25 µg/mL anti-h$VEGF_{165}a$ per well. The plate was sealed with parafilm and incubated overnight on the shaker at room temp. Each well was aspirated and washed with Wash Buffer (200 µL PBS-Tween 0.05%), two times for a total of three washes. After the last wash, remaining Wash Buffer was removed by inverting the plate and blotting it against clean paper towels. Plates were blocked by adding 100 µL of Reagent Diluent (1% BSA/PBS) to each well and incubated at room temp on a shaker for 2 hours. The aspiration/wash step was repeated. 100 µL of standards or samples in 1% BSA/PBS were added to each well, covered with parafilm and incubated 2 hours at room temperature. The aspiration/wash was repeated and 100 µL of 100 ng/mL of Detection Antibody (BAF293), diluted in Reagent Diluent, was added to each well which were covered with parafilm and incubated 2 hours at room temperature. The aspiration/wash was repeated and 100 µL of the working dilution of Streptavidin-HRP (1:200 dilution) was added to each well. The plate was covered and incubated for 30 minutes at room temperature. The plate was washed and 100 of Substrate Solution (1:1 of A:B from DY999) added to each well and incubated for 20-60 minutes at room temperature. 50 µL of Stop Solution (1M HCl) was added to each well. The optical density of each well was measured immediately, using a microplate reader set to 450 nm.

Melanin Binding Assay

1 µg/mL of test compounds in PBS with 1% DMSO were incubated with 1 mg/mL melanin for 1 hr at 37° C. Solutions were then spun at 15 kg for 15 mins and supernatant collected and compounds extracted in methanol. They were then subjected to mass spectrometry for quantitation.

Rabbit Pharmacokinetic Study

Rabbits were treated with a single 50 µL eye drop of pazopanib at 80 µg/ml (maximum limit of solubility) and compound R at 500 µg/mL in the initial eye drop formulation containing 1% hydroxypropyl methyl cellulose, 0.2% tyloxapol, 3.4% dextrose, 0.006% benzalkonium chloride, and 0.025% ethylenediaminetetraacetic acid with 1% DMSO in PBS or with a single 50 µL eye drop of compound 1 at 500 µg/mL in the eye drop formulation containing 7% poly-oxyl-40-stearate and 4% dextrose in PBS. No difference between the eye drop formulations was confirmed in a separate study. Rabbits were killed at the indicated time points after the eye drop, blood and eyes taken, and the retina dissected from the choroid and sclera, incisions made, and laid out flat. Retina, RPE/choroid and sclera eye compartments were dissected into 7 different areas. All samples were weighed. Compound was extracted by reverse phase extraction from the retina and choroid/sclera samples and the plasma as above, and amount determined by mass spectrometry in different areas of the eye and in the blood. Amounts per milligram of tissue were calculated for compound R, compound 1 and pazopanib for each sample, and averaged.

Scleral permeability was measured using a modified Ussing chamber assembly in the initial eye drop formulation containing 1% hydroxypropyl methyl cellulose, 0.2% tyloxapol, 3.4% dextrose, 0.006% benzalkonium chloride, and 0.025% ethylenediaminetetraacetic acid with 1% DMSO in PBS (pH 7.4). Porcine excised eye tissues were mounted in the chambers such that the episcleral side faced the donor chamber and the retinal side faced the receiver chamber. The chambers were filled with equal volumes of eye drop formulation, with (donor side) or without (receiver side) 10 µg/mL compound. After 24 hours tissue was removed from the chamber and the receiver side ("vitreous") sampled. Tissue was dissected into sclera, choroid/RPE, and retina and homogenised. A tracer (SPHINX7; WO 2015/159103) was added, and tissue extracted by acetonitrile extraction as described in Batson et al (2017). Compounds were then analysed by mass spectrometry as described in Batson et al (2017).

Non-human primate pharmacokinetic study Cynomolgus monkeys were treated bidaily for 20 days with 35 µL eye drops of compound 1 at 0.5 mg/mL, 1.0 mg/mL or 1.5 mg/ml as indicated, in the eye drop formulation containing 7% poly-oxyl-40-stearate and 4% dextrose in PBS. Blood and aqueous samples were collected 1 h, 4 h, 8 h, 10 h and 14 h after eye drop administration on day 1 and at the end of the study. 1 h after the final eye drop on day 21, the animals were euthanised and ocular tissues and blood were collected. The retina was dissected from the choroid and sclera, incisions made, and laid out flat. Retina, RPE/choroid and sclera eye compartments were dissected into 7 different areas. All samples were weighed. Compound was extracted by reverse phase extraction from the retina and choroid/sclera samples and the plasma as above, and amount determined by mass spectrometry in different areas of the eye and in the blood. Amounts per milligram of tissue or nM for aqueous and blood were calculated for each sample, and averaged.

Retina sections sampled from half of the eye were homogenised in NP40 lysis buffer as described in Gammons et al., 2013. The extracts were then immunoblotted using either rabbit anti-panVEGF (Santa Cruz A20 sc-152; 1:500) or mouse anti-$VEGFi_{65}b$ (MAB3045; R&D; 1:500).

Results

The following examples substantiate the invention. The compounds of the invention are potent SRPK1 inhibitors and have high ocular permeability.

We have previously determined that SRPK1 inhibitors could be generated that were highly potent ($IC_{50}<10^{-8}M$), were anti-angiogenic in mouse models of choroidal neovascularisation, and could penetrate through the sclera to the choroid and retinal pigmented epithelial layer of rabbits. We considered that maximising the penetration of the molecule to the eye is critical for the development of effective topical therapeutics. The compounds of the invention have improved properties over the compounds described in WO 2014/060763 and WO 2017/064512, and are useful for the topical treatment of ocular neovascularization and hyperpermeability disorders that are dependent on over-expression of the anti-angiogenic VEGF isoforms.

Permeability

To determine whether compounds could get across the sclera of a larger animal, porcine sclera was clamped between two chambers and compounds were added to the sclera with eye drop formulation added to the bottom chamber and compounds added to the top chamber. After 24 hours, the fluid from the bottom chamber (vitreous) and the retinal tissue was isolated and compounds purified by methanol or acetonitrile extraction and HPLC. This highlighted that compounds could be generated that were both highly permeable and highly potent. In particular it was clear that the novel compounds of the invention (as shown for compounds 1-3) have a surprisingly high permeability, much higher than the permeability of SPHINX31 (FIG. 1; Table 1), and were still highly potent (Table 2). This was particularly surprising as chemically similar compounds lacking the methyl group on the pyrazole, for example previously described Compound R had considerably lower permeability (FIG. 1). Furthermore, the compounds of the invention are also substantially more permeable than compounds that have previously been shown to inhibit VEGF signalling through VEGFR2 but failed in clinical trials due to lack of exposure (pazopanib, regorafenib, LHA510), and greater than compounds that have been used effectively as topical eye drops but act in the anterior segment (indomethacin, celecoxib)—see FIG. 1.

TABLE 1

| Porcine permeability | Permeability ($\times 10^{-6}$ cm/s) |
| --- | --- |
| Compound 1 | 0.0670 |
| Compound 2 | 0.0442 |
| Compound 3 | 0.0675 |

Figure 2:
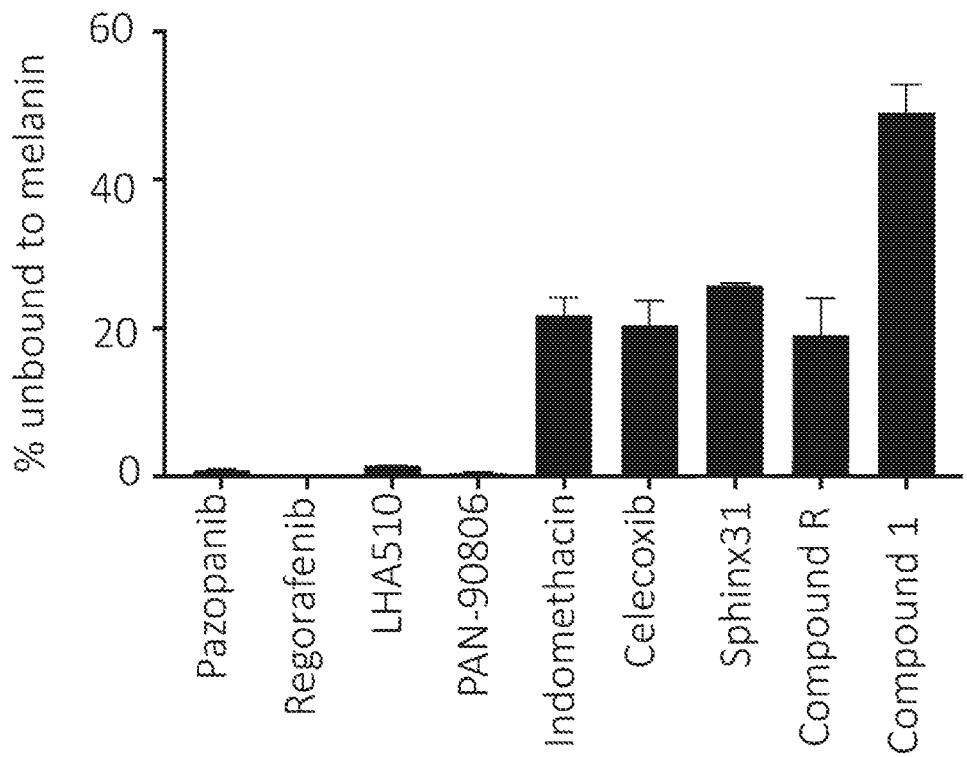
FIG. 2 shows the amount of compound unbound to melanin.

Melanin binding has been proposed to be important for bioavailability of compounds in the eye. The melanin binding of the compounds of the invention was measured and determined that they are substantially less bound to melanin than previous SRPK1 inhibitors (SPHINX31; WO 2015/159103, and Compound R), and previous VEGFR2 inhibitors that had been tried as anti-angiogenic agents. (FIG. 2).

Figure 3A:
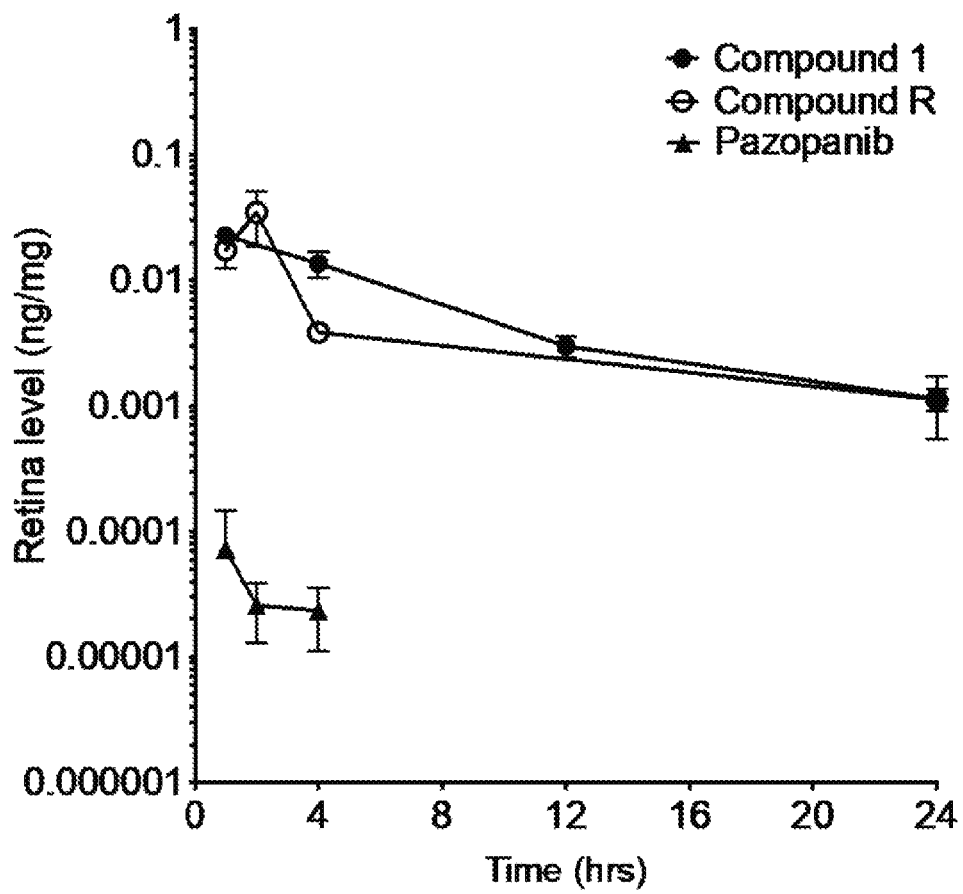
FIG. 3a shows the penetration of compound 1 to the retina in comparison to a chemically similar compound (N-(2-(4-((1H-pyrazol-3-yl)methyl)piperazin-1-yl)-5-(trifluoromethyl)-phenyl)-5-(tetrahydro-2H-pyran-4-yl)furan-2-carboxamide termed compound R) and to pazopanib.
Figure 3B:
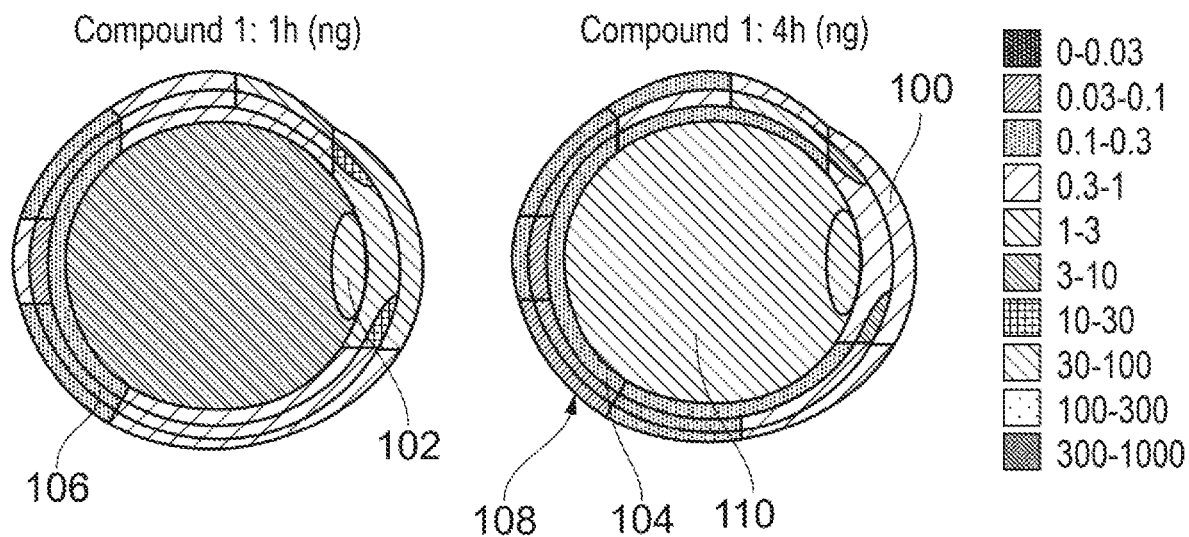
FIG. 3b shows the distribution of Compound 1 through various eye tissues.
Figure 4:
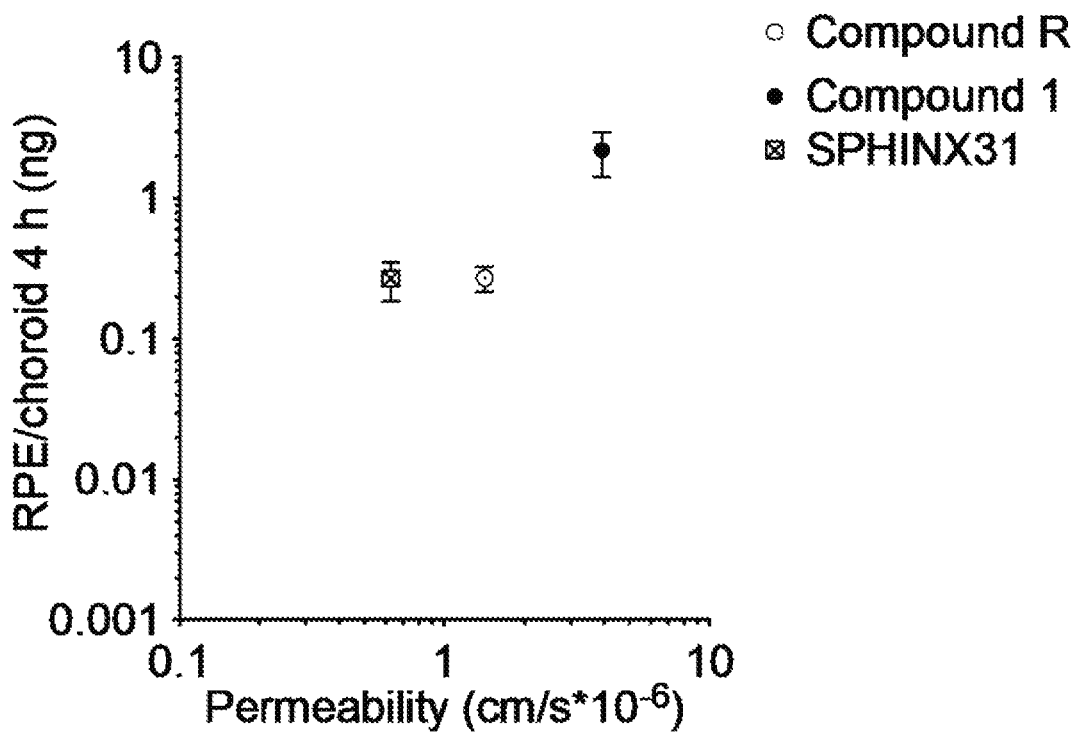
FIG. 4 shows the relationship between ex vivo permeability and amount of compound found in the retina for compound 1, Compound R and SPHINX31 (WO 2015/159103)

To determine if the compounds could access the RPE of an animal with a large eye, a rabbit was exposed to 500 µg/mL of the compound as an eye drop and the concentrations in the retina, sclera, vitreous and other eye tissues (cornea); lens; RPE/choroid were measured. (FIG. 3a). After 1, 4, 12 or 24 hours the animal was killed and the eyes harvested. Individual sections of cornea (100), lens (102), and vitreous (110), along with sections of sclera (108), RPE/choroid (106) and retina (104) from the rear portions of the eye were then assayed for compound. Retinal penetration was seen for the compounds of the invention. The results obtained for Compound 1 are shown in FIGS. 3a and 3b. Permeability was superior to the permeability of previously studied SRPK1 inhibitors such as SPHINX31 and had a better sustained penetration (e.g. at 4 hrs) than chemically similar molecules such as Compound R (FIG. 4).

SRPK1 Selectivity

The inhibitory activity of the compounds of the invention on SRPK1 was measured with data presented in Table 2. All compounds are potent inhibitors of SPRK1, and were highly selective for SRPK1 when tested against a panel of kinases at 1 µM.

TABLE 2

| $IC_{50}$ | SRPK1 (nM) |
| --- | --- |
| Compound 1 | 4 |
| Compound 2 | 10 |
| Compound 3 | 35 |

Compound 1 Switches Expression to the Anti-Angiogenic Isoforms in Human Cells.

Figure 5:
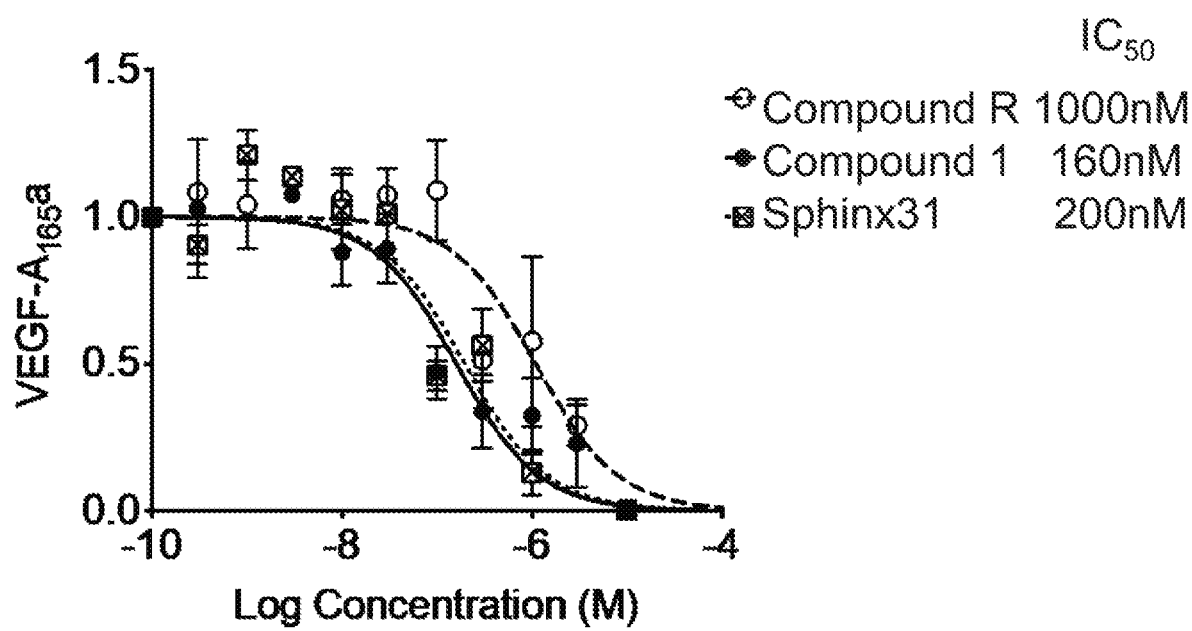
FIG. 5 shows from an ELISA that compound 1 switches alternative splicing to decrease VEGF-$A_{165}$a isoform expression in retinal pigmented epithelial cell line.
Figure 6A:
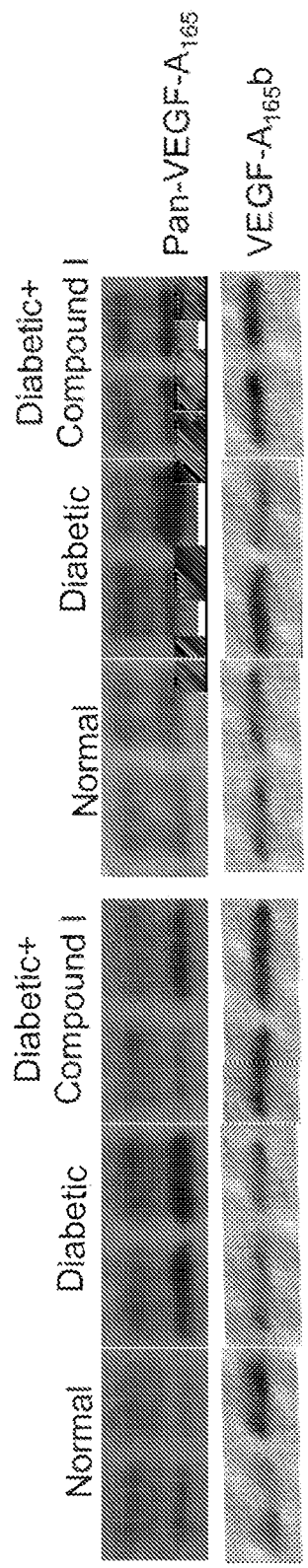
FIG. 6a shows the results of bidaily eye drops of compound 1 for 28 days on VEGF expression in diabetic rats measured by Western blot.
Figure 6D:
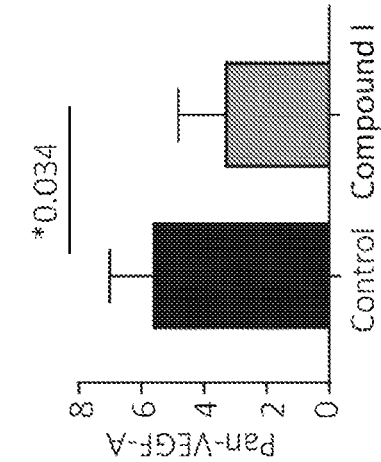
FIG. 6d shows that the proportion of VEGF-$A_{165}$b to total VEGF was increased by compound 1.
Figure 6C:
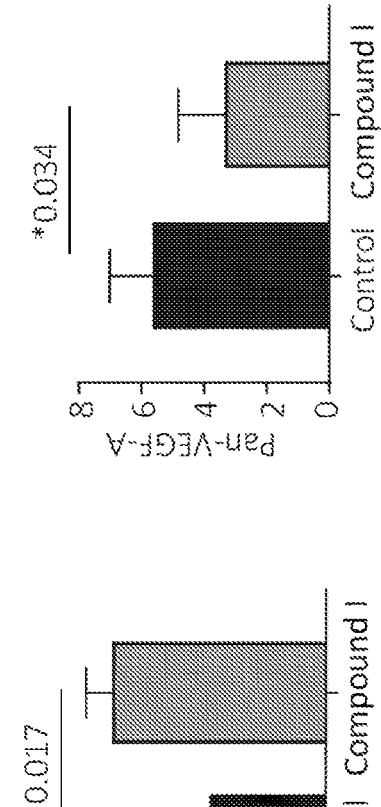
FIG. 6b shows that total VEGF is reduced, FIG. 6c that VEGF-$A_{165}$b is increased
Figure 6B:
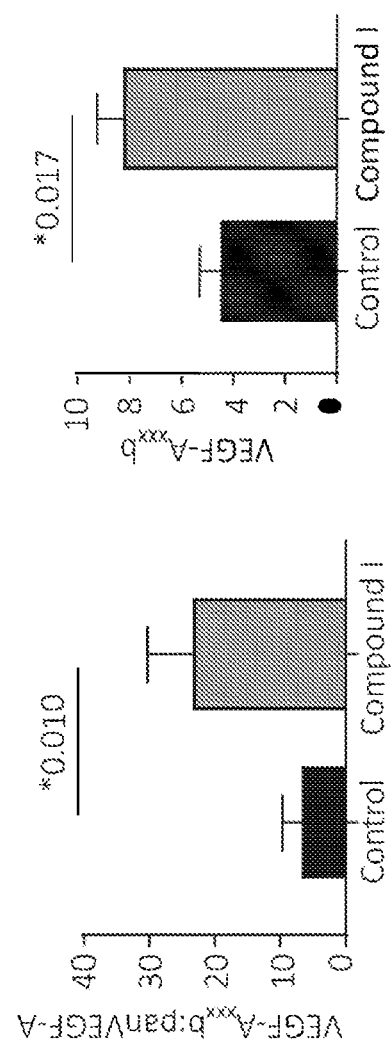

To determine whether compound 1 could switch splicing of VEGF isoforms, VEGF was measured in retinal pigmented epithelial cells by isoform specific ELISA. FIG. 5 shows that treatment with compound 1 reduces expression of the pro-angiogenic VEGF-$A_{165}$a isoform in a dose dependent manner.

Compound 1 Switches Expression Away from the Pro-Angiogenic VEGF Isoforms in Rat Diabetic Retinopathy Models.

To determine whether compound 1 could effectively switch the splicing of VEGF in a model of diabetes we used the STZ model of diabetes in Norway Brown rats. Diabetic animals were treated with twice daily eye drops of compound 1 for four weeks and killed, and the retina dissected. Protein was extracted and subjected to immunoblotting for VEGF-$A_{165}$b and panVEGF. FIGS. 6a to 6d show that while in diabetic animals total VEGF was upregulated but VEGF-$A_{165}$b was downregulated compared with healthy rats, this was reversed by treatment with Compound 1.

Compound 1 Inhibits Choroidal Neovascularisation In Vivo.

Figure 7A:
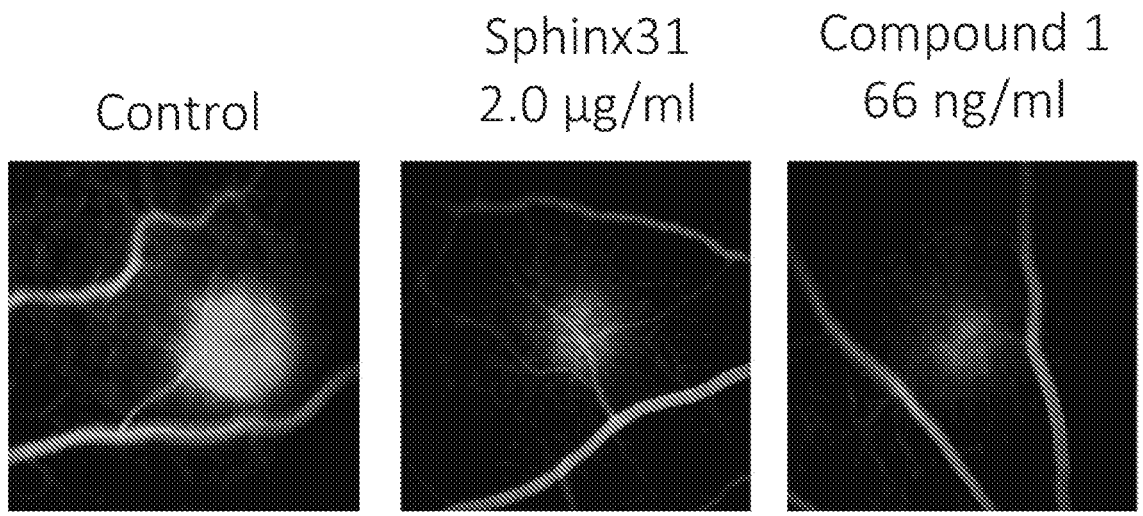
FIG. 7a shows fluorescein angiography images and FIG. 7b graphically presents the same data demonstrating that compound 1 has the same anti-angiogenic activity on lesion size as reference compounds in the laser-induced mouse model of CNV.
Figure 7B:
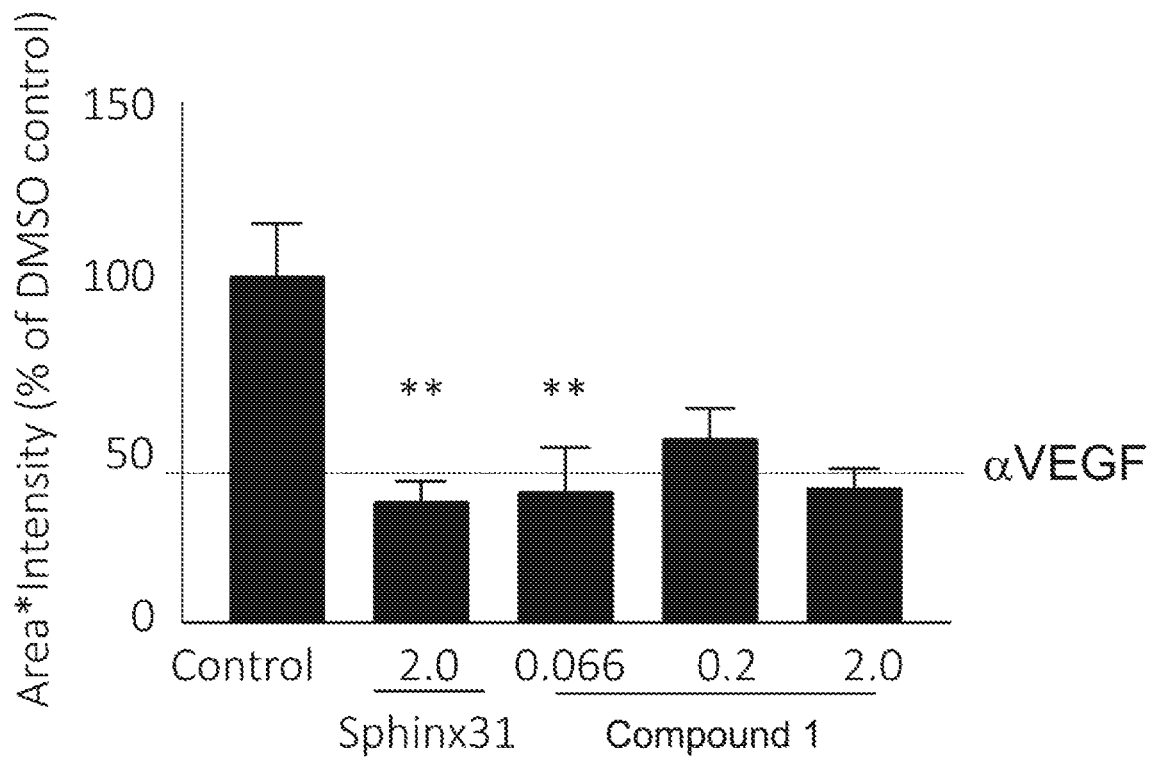

We have previously shown that SRPK1 inhibition by SPHINX31 was anti-angiogenic in mouse models of choroidal neovascularisation, as eye drops with a maximum effect at 2 µg/ml, as these compounds are relatively lipophilic and have high penetrance into the eye. We therefore tested the effect of compound 1 as an eyedrop in this same model. Compound 1 significantly inhibited choroidal neovascularisation at 0.066 µg/mL (FIG. 7b).

Compound 1 Penetrates at Effective Doses in Non-Human Primates

Figure 8A:
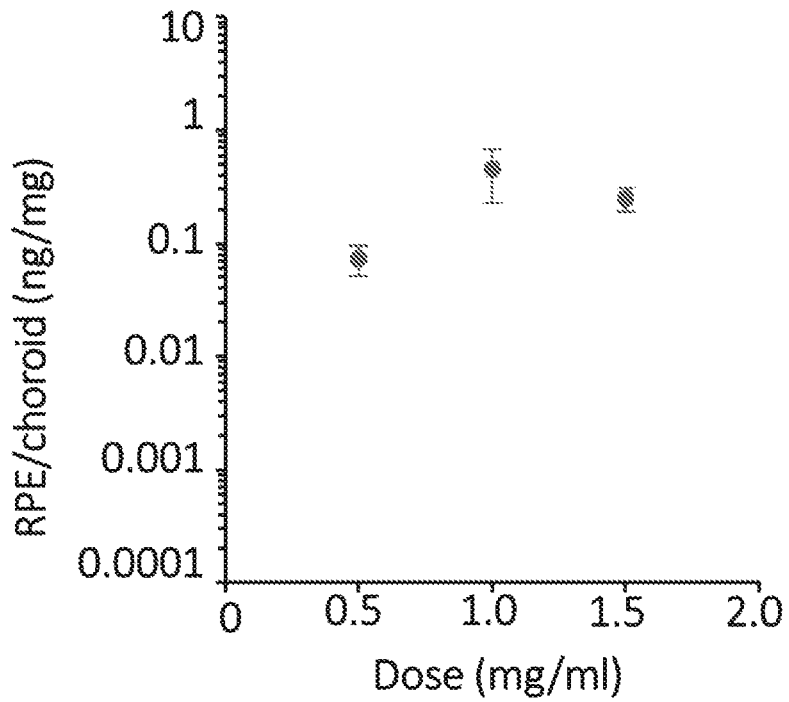
FIG. 8a shows the amount of compound 1 found in the retina of cynomolgous monkeys treated bidaily with eye drops at 0.5 mg/mL, 1.0 mg/mL and 1.5 mg/mL for three weeks.
Figure 8B:
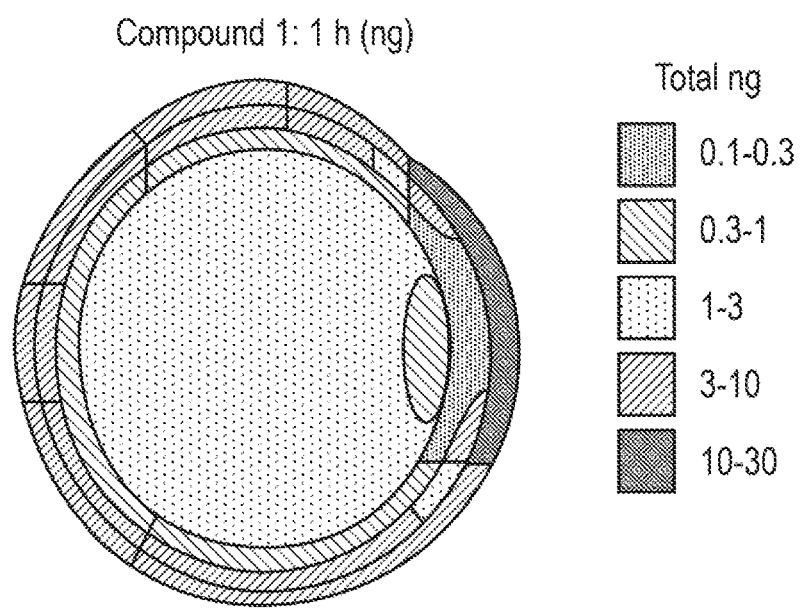
FIG. 8b is a colour intensity drawing of the amounts of compound 1 in different tissues in the eye.
Figure 9:
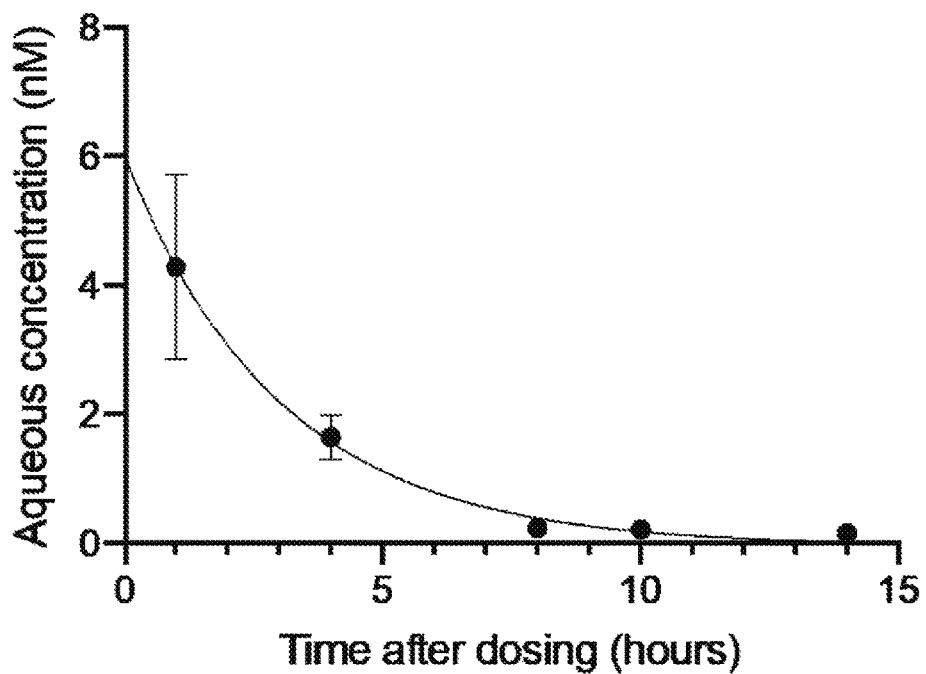
FIG. 9 shows the concentration of compound 1 in the aqueous after single eye drops of compound 1 at different doses.
Figure 10A:
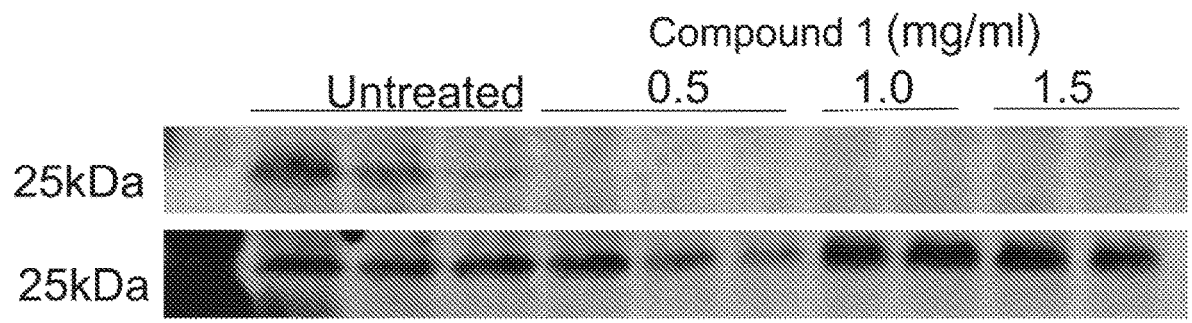
FIG. 10a shows that VEGF levels in the retina change in monkeys treated with Compound 1 as eye drops (top: Pan VEGF-$A_{165}$; bottom: VEGF-$A_{165}$b)
Figure 10B:
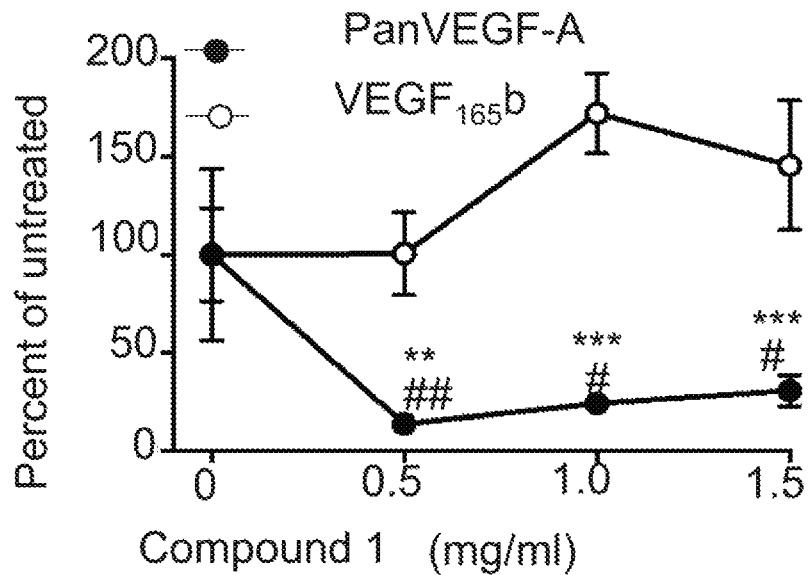
FIG. 10b shows the intensity of western blot bands relative to the mean of the untreated on each blot (treated, N=3 per group, N=6 eyes per group, untreated N=6 animals, N=12 eyes, mean±SEM), Two-Way ANOVA p<0.001, post-hoc BKY test for FDR =p<0.01, *=p<0.001 compared with VEGF165b, ##=p<0.01, ###=p<0.001 compared with untreated.
Figure 10C:
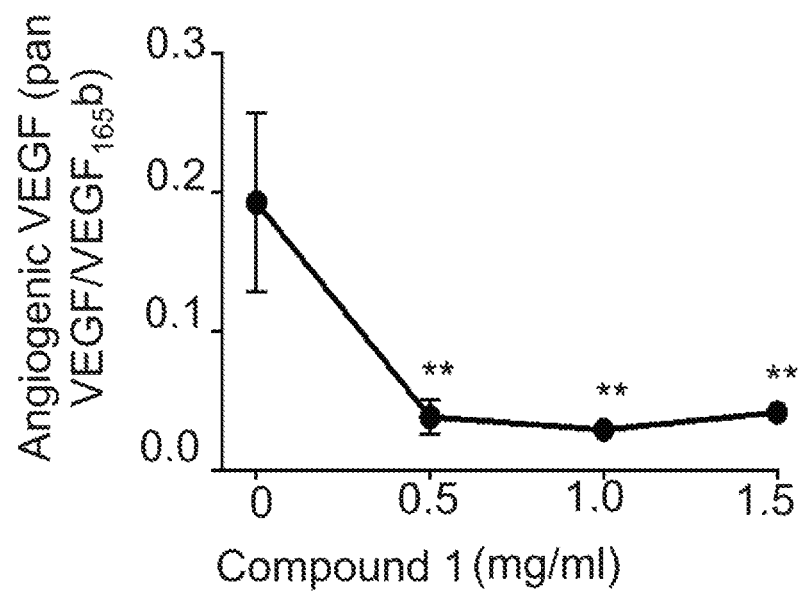
FIG. 10c shows the ratio of panVEGF to VEGF$_{165}$b for each sample—a reduction is a switch to a less angiogenic state. One way ANOVA p<0.01, **=p<0.01 compared with untreated (Holm Sidak post hoc).

To determine whether compound 1 could penetrate into the retina of primates we dosed cynomologous monkeys with 0.5, 1.0 or 1.5 mg/mL compound 1 twice a day for 21 days. FIG. 8 shows that even in primate retina significant concentrations of compound 1 were seen in the retina, choroid, vitreous and other tissues of the eye (FIGS. 8a and 8b) at concentrations calculated to be much higher than that required for efficacy based on the mouse model. Aqueous taps and plasma samples were taken during the treatment and compound 1 measured in the fluid. Significant concentrations were seen at all three doses with the half-life in the aqueous calculated to be 2 hours after administration of 1.5 mg/mL (FIG. 9). To determine if these doses were sufficient to inhibit angiogenic VEGF-A isoform expression, retinal tissue was subjected to immunoblotting using pan-VEGF or VEGF-$A_{165}$b antibodies. FIG. 10a shows that in monkeys treated with compound 1 as eye drops, VEGF levels in the retina change, FIG. 10b shows that total VEGF levels are decreased after 3 weeks bidaily dosing, and VEGF-$A_{165}$b levels do not decrease and increase at 1 mg/ml, and FIG. 10c shows that the ratio of angiogenic to anti-angiogenic VEGF-A decreases in the retina of monkeys dosed with compound 1.

REFERENCES

Bressler, S., Bressler, N. M., Clemons, T., Ferris, F. L., Milton, R. C., Klien, R., Klien, B. and Age-Related Eye Dis Study, G. (2004) 'Ocular risk factors for developing neovascular AMD in the fellow eyes of patients with unilateral neovascular AMD', *Investigative Ophthalmology & Visual Science*, 45, U924-U924.

Ferris, F. L., Fine, S. L. and Hyman, L. (1984) 'Age-related macular degeneration and blindness due to neovascular maculopathy', *Archives of Ophthalmology*, 102(11), 1640-1642.

Patz, A., Fine, S. L., Finkelstein, D. and Yassur, Y. (1977) 'Diseases of macula—diagnosis and management of choroidal neovascularization', *Transactions American Academy of Ophthalmology and Otolaryngology*, 83(3), 468-475.

Fine, S. L., Berger, J. W., Maguire, M. G. and Ho, A. C. (2000) 'Drug therapy: Age-related macular degeneration', *New England Journal of Medicine*, 342(7), 483-492.

Campochiaro, P. A., Nguyen, Q. D., Shah, S. M., Klein, M. L., Holz, E., Frank, R. N., Saperstein, D. A., Gupta, A., Stout, J. T., Macko, J., DiBartolomeo, R. and Wei, L. L. (2006) 'Adenoviral vector-delivered pigment epithelium-derived factor for neovascular age-related macular degeneration: Results of a phase I clinical trial', *Human Gene Therapy*, 17(2), 167-176.

Dvorak, H. F., Brown, L. F., Detmar, M. and Dvorak, A. M. (1995) 'Vascular-permeability factor vascular endothelial growth-factor, microvascular hyperpermeability, and angiogenesis', *American Journal of Pathology*, 146(5), 1029-1039.

Spilsbury, K., Garrett, K. L., Shen, W. Y., Constable, I. J. and Rakoczy, P. E. (2000) 'Overexpression of vascular endothelial growth factor (VEGF) in the retinal pigment epithelium leads to the development of choroidal neovascularization', *American Journal of Pathology*, 157(1), 135-144.

Anderson, D. H., Mullins, R. F., Hageman, G. S. and Johnson, L. V. (2002) 'Perspective—A role for local inflammation in the formation of drusen in the aging eye', *American Journal of Ophthalmology*, 134(3), 411-431.

Das, A., Fanslow, W., Cerretti, D., Warren, E., Talarico, N. and McGuire, P. (2003) 'Angiopoietin/Tek interactions regulate MMP-9 expression and retinal neovascularization', *Laboratory Investigation*, 83(11), 1637-1645.

Leung, D. W., Cachianes, G., Kuang, W. J., Goeddel, D. V. and Ferrara, N. (1989) 'Vascular endothelial growth-factor is a secreted angiogenic mitogen', *Science*, 246 (4935), 1306-1309.

Jingjing, L., Xue, Y., Agarwal, N. and Roque, R. S. (1999) 'Human Muller cells express VEGF183, a novel spliced variant of vascular endothelial growth factor', *Iovs*, 40(3), 752-759.

Houck, K. A., Ferrara, N., Winer, J., Cachianes, G., Li, B. and Leung, D. W. (1991) 'The vascular endothelial growth-factor family—identification of a 4th molecular-species and characterization of alternative splicing of rna', *Molecular Endocrinology*, 5(12), 1806-1814.

Mineur, P., Colige, A. C., Deroanne, C. F., Dubail, J., Kesteloot, F., Habraken, Y., Noel, A., Voo, S., Waltenberger, J., Lapiere, C. M., Nusgens, B. V. and Lambert, C. A. (2007) 'Newly identified biologically active and proteolysis-resistant VEGF-A isoform $VEGF_{111}$ is induced by genotoxic agents', *Journal of Cell Biology*, 179(6), 1261-1273.

Tischer, E., Gospodarowicz, D., Mitchell, R., Silva, M., Schilling, J., Lau, K., Crisp, T., Fiddes, J. C. and Abraham, J. A. (1989) 'Vascular endothelial growth-factor—a new member of the platelet-derived growth-factor gene family', *Biochemical and Biophysical Research Communications*, 165(3), 1198-1206.

Neufeld, G., Cohen, T., Gengrinovitch, S. and Poltorak, Z. (1999) 'Vascular endothelial growth factor (VEGF) and its receptors', *Faseb Journal*, 13(1), 9-22.

Bates, D. O., Cui, T. G., Doughty, J. M., Winkler, M., Sugiono, M., Shields, J. D., Peat, D., Gillatt, D. and Harper, S. J. (2002) 'VEGF(165)b, an inhibitory splice variant of vascular endothelial growth factor, is down-regulated in renal cell carcinoma', *Cancer Research*, 62(14), 4123-4131.

Woolard, J., Wang, W. Y., Bevan, H. S., Qiu, Y., Morbidelli, L., Pritchard-Jones, R. O., Cui, T. G., Sugiono, M., Waine, E., Perrin, R., Foster, R., Digby-Bell, J., Shields, J. D., Whittles, C. E., Mushens, R. E., Gillatt, D. A., Ziche, M., Harper, S. J. and Bates, D. O. (2004) 'VEGF(165)b, an inhibitory vascular endothelial growth factor splice variant: Mechanism of action, in vivo effect on angiogenesis and endogenous protein expression', *Cancer Research*, 64(21), 7822-7835.

Perrin, R. M., Konopatskaya, O., Qiu, Y., Harper, S., Bates, D. O. and Churchill, A. J. (2005) 'Diabetic retinopathy is associated with a switch in splicing from anti- to pro-angiogenic isoforms of vascular endothelial growth factor', *Diabetologia*, 48(11), 2422-2427.

Varey, A. H. R., Rennel, E. S., Qiu, Y., Bevan, H. S., Perrin, R. M., Raffy, S., Dixon, A. R., Paraskeva, C., Zaccheo, O., Hassan, A. B., Harper, S. J. and Bates, D. O. (2008) 'VEGF(165)b, an antiangiogenic VEGF-A isoform, binds and inhibits bevacizumab treatment in experimental colorectal carcinoma: balance of pro- and antiangiogenic VEGF-A isoforms has implications for therapy', *British Journal of Cancer*, 98(8), 1366-1379.

Pritchard-Jones, R. O., Dunn, D. B. A., Qiu, Y., Varey, A. H. R., Orlando, A., Rigby, H., Harper, S. J. and Bates, D. O. (2007) 'Expression of VEGF(xxx)b, the inhibitory isoforms of VEGF, in malignant melanoma', *British Journal of Cancer*, 97(2), 223-230.

Hua, J., Spee, C., Kase, S., Rennel, E. S., Magnussen, A. L., Qiu, Y., Varey, A., Dhayade, S., Churchill, A. J., Harper, S. J., Bates, D. O. and Hinton, D. R. (2010) 'Recombinant Human VEGF(165)b Inhibits Experimental Choroidal Neovascularization', *Investigative Ophthalmology & Visual Science*, 51(8), 4282-4288.

Magnussen, A. L., Rennel, E. S., Hua, J., Bevan, H. S., Long, N. B., Lehrling, C., Gammons, M., Floege, J., Harper, S. J., Agostini, H. T., Bates, D. O. and Churchill, A. J. (2010) 'VEGF-A(165)b Is Cytoprotective and Anti-angiogenic in the Retina', *Investigative Ophthalmology & Visual Science*, 51(8), 4273-4281.

Rosenfeld, P. J., Rich, R. M. and Lalwani, G. A. (2006) 'Ranibizumab: Phase III clinical trial results', *Ophthalmology clinics of North America*, 19(3), 361-72.

Brown, D. M., Kaiser, P. K., Michels, M., Soubrane, G., Heier, J. S., Kim, R. Y., Sy, J. P., Schneider, S. and Grp, A. S. (2006) 'Ranibizumab versus verteporfin for neovascular age-related macular degeneration', *New England Journal of Medicine*, 355(14), 1432-1444.

Brown, D. M., Michels, M., Kaiser, P. K., Heier, J. S., Sy, J. P. and Ianchulev, T. (2009) 'Ranibizumab versus Verteporfin Photodynamic Therapy for Neovascular Age-Related Macular Degeneration: Two-Year Results of the ANCHOR Study', *Ophthalmology*, 116(1), 57-65.

Schmidt-Erfurth, U., Eldem, B., Guymer, R., Korobelnik, J.-F., Schlingemann, R. O., Axer-Siegel, R., Wiedemann, P., Simader, C., Gekkieva, M., Weichselberger, A. and Grp, E. S. (2011) 'Efficacy and Safety of Monthly versus Quarterly Ranibizumab Treatment in Neovascular Age-related Macular Degeneration: The EXCITE Study', *Ophthalmology*, 118(5).

Good, T. J. and Kahook, M. Y. (2010) 'The role of endothelin in the pathophysiology of glaucoma', *Expert Opinion on Therapeutic Targets*, 14(6), 647-654.

Jager, R. D., Aiello, L. P., Patel, S. C. and Cunningham, E T. (2004) 'Risks of intravitreous injection: A comprehensive review', *Retina-the Journal of Retinal and Vitreous Diseases*, 24(5), 676-698.

Nowak, D. G., Amin, E. M., Rennel, E. S., Hoareau-Aveilla, C., Gammons, M., Damodoran, G., Hagiwara, M., Harper, S. J., Woolard, J., Ladomery, M. R. and Bates, D. O. (2010) 'Regulation of Vascular Endothelial Growth Factor (VEGF) Splicing from Pro-angiogenic to Anti-angiogenic Isoforms a novel therapeutic strategy for angiogenesis', *Journal of Biological Chemistry*, 285(8), 5532-5540.

Amin, E. M., Oltean, S., Hua, J., Gammons, M. V. R., Hamdollah-Zadeh, M., Welsh, G. I., Cheung, M.-K., Ni, L., Kase, S., Renne, E. S., Symonds, K. E., Nowak, D. G., Royer-Pokora, B., Saleem, M. A., Hagiwara, M., Schumacher, V. A., Harper, S. J., Hinton, D. R., Bates, D. O. and Ladomery, M. R. (2011) 'WT1 Mutants Reveal SRPK1 to Be a Downstream Angiogenesis Target by Altering VEGF Splicing', *Cancer Cell*, 20(6), 768-780.

Sanford, J. R., Ellis, J. D., Cazalla, D. and Caceres, J. F. (2005a) 'Reversible phosphorylation differentially affects nuclear and cytoplasmic functions of splicing factor 2/alternative splicing factor', *Proceedings of the National Academy of Sciences of the United States of America*, 102(42), 15042-15047.

Nowak, D. G., Woolard, J., Amin, E. M., Konopatskaya, O., Saleem, M. A., Churchill, A. J., Ladomery, M. R., Harper, S. J. and Bates, D. O. (2008) 'Expression of pro- and anti-angiogenic isoforms of VEGF is differentially regulated by splicing and growth factors', *Journal of Cell Science*, 121(20), 3487-3495.

Doukas, J., Mahesh, S., Umeda, N., Kachi, S., Akiyama, H., Yokoi, K., Cao, J., Chen, Z., Dellamary, L., Tam, B., Racanelli-Layton, A., Hood, J., Martin, M., Noronha, G., Soll, R. and Campochiaro, P. A. (2008) 'Topical administration of a multi-targeted kinase inhibitor suppresses choroidal neovascularization and retinal edema', *Journal of Cellular Physiology*, 216(1), 29-37.

Fukuhara, T., Hosoya, T., Shimizu, S., Sumi, K., Oshiro, T., Yoshinaka, Y., Suzuki, M., Yamamoto, N., Herzenberg, L. A. and Hagiwara, M. (2006) 'Utilization of host SR protein kinases and RNA-splicing machinery during viral replication', *Proceedings of the National Academy of Sciences of the United States of America*, 103(30), 11329-11333.

Rennel, E. S., Regula, J. T., Harper, S. J., Thomas, M., Klein, C. and Bates, D. O. (2011) 'A Human Neutralizing Antibody Specific to Ang-2 Inhibits Ocular Angiogenesis', *Microcirculation*, 18(7).

Aubol, B. E., Chakrabarti, S., Ngo, J., Shaffer, J., Nolen, B., Fu, X. D., Ghosh, G. and Adams, J. A. (2003) 'Processive phosphorylation of alternative splicing factor/splicing factor 2', *Proceedings of the National Academy of Sciences of the United States of America*, 100(22), 12601-12606.

Velazquez-Dones, A., Hagopian, J. C., Ma, C. T., Zhong, X. Y., Zhou, H. L., Ghosh, G., Fu, X. D. and Adams, J. A. (2005) 'Mass spectrometric and kinetic analysis of ASF/SF2 phosphorylation by SRPK1 and Clk/Sty', *Journal of Biological Chemistry*, 280(50), 41761-41768.

Ngo, J. C. K., Chakrabarti, S., Ding, J. H., Velazquez-Dones, A., Nolen, B., Aubol, B. E., Adams, J. A., Fu, X. D. and Ghosh, G. (2005) 'Interplay between SRPK and Clk/Sty kinases in phosphorylation of the splicing factor ASF/SF2 is regulated by a docking motif in ASF/SF2', *Molecular Cell*, 20(1), 77-89.

Xu, J., Dou, T., Liu, C., Fu, M., Huang, Y., Gu, S., Zhou, Y. and Xie, Y. (2011) 'The evolution of alternative splicing exons in vascular endothelial growth factor A', *Gene*, 487(2).

Caires, K. C., de Avila, J. M., Cupp, A. S. and McLean, D. J. (2012) 'VEGFA Family Isoforms Regulate Spermatogonial Stem Cell Homeostasis in Vivo', *Endocrinology*, 153(2).

Zhao, M., Shi, X., Liang, J., Miao, Y., Xie, W., Zhang, Y. and Li, X. (2011) 'Expression of pro- and anti-angiogenic isoforms of VEGF in the mouse model of oxygen-induced retinopathy', *Experimental Eye Research*, 93(6), 921-926.

Harris, S., Craze, M., Newton, J., Fisher, M., Shima, D. T., Tozer, G. M. and Kanthou, C. (2012) 'Do Anti-Angiogenic VEGF (VEGF b) Isoforms Exist? A Cautionary Tale', *Plos One*, 7(5).

McFee, R. M., Rozell, T. G. and Cupp, A. S. (2012) 'The balance of proangiogenic and antiangiogenic VEGFA isoforms regulate follicle development', *Cell and Tissue Research*, 349(3).

Ishida, S., Usui, T., Yamashiro, K., Kaji, Y., Amano, S., Ogura, Y., Hida, T., Oguchi, Y., Ambati, J., Miller, J. W., Gragoudas, E. S., Ng, Y. S., D'Amore, P. A., Shima, D. T. and Adamis, A. P. (2003) 'VEGF$_{(164)}$-mediated inflammation is required for pathological, but not physiological, ischemia-induced retinal neovascularization', *Journal of Experimental Medicine*, 198(3), 483-489.

Geroski, D. H. and Edelhauser, H. F. (2000) 'Drug delivery for posterior segment eye disease', *Investigative Ophthalmology & Visual Science*, 41(5), 961-964.

Keyt, B. A., Nguyen, H. V., Berleau, L. T., Duarte, C. M., Park, J., Chen, H. and Ferrara, N. (1996) 'Identification of vascular endothelial growth factor determinants for binding KDR and FLT-1 receptors—Generation of receptor-selective VEGF variants by site-directed mutagenesis', *Journal of Biological Chemistry*, 271(10), 5638-5646.

Stalmans, I., Ng, Y. S., Rohan, R., Fruttiger, M., Bouche, A., Yuce, A., Fujisawa, H., Hermans, B., Shani, M., Jansen, S., Hicklin, D., Anderson, D. J., Gardiner, T., Hammes, H. P., Moons, L., Dewerchin, M., Collen, D., Carmeliet, P. and D'Amore, P. A. (2002) 'Arteriolar and venular patterning in retinas of mice selectively expressing VEGF isoforms', *Journal of Clinical Investigation*, 109(3).

Gammons, M. V., Dick, A. D., Harper, S. J., Bates, D. O. (2013) SRPK1 Inhibition Modulates VEGF Splicing to Reduce Pathological Neovascularization in a Rat Model of Retinopathy of Prematurity Invest. *Ophthalmol. Vis. Sci.* vol. 54(8) 5797-5806.

Gammons, M. V., Fedorov, O., Ivison, D., Du, C., Clark, T., Hopkins, C., Hagiwara, M., Dick, A. D., Cox, R., Harper, S. J., Hancox, J. C. and Bates, D. O. (2013) Topical Antiangiogenic SRPK1 Inhibitors Reduce Choroidal Neovascularization in Rodent Models of Exudative AMD Invest. *Ophthalmol. Vis. Sci.* 54(9) 6052-6062.

Federov O, Niesen F H, Knapp S. Kinase Inhibitor Selectivity Profiling Using Differential Scanning Fluorimetry. In: Kuster B, ed. Kinase Inhibitors: Methods and Protocols: Springer, 2011:109-18.

Carter J G, Gammons M V, Damodaran G, Churchill A J, Harper S J, Bates D O. (2015) The carboxyl terminus of VEGF-A is a potential target for anti-angiogenic therapy. Angiogenesis 18(1), 23-30.

Chomczynski, P., and Sacchi, N. Single-step method of RNA isolation by acid quanidinium thiocyanate phenol chloroform extraction. Anal. Biochem., 162: 156-159, 1987.

Batson, J., Toop, H. D., Redondo, C., Babaei-Jadidi, R., Chaikuad, A., Wearmouth, S. F., Gibbons, B., Allen, C., Tallant, C., Zhang, J., Du, C., Hancox, J. C., Hawtrey, T., Da Rocha, J., Griffith, R., Knapp, S., Bates, D. O., Morris, J. C., Development of Potent, Selective SRPK1 Inhibitors as Potential Topical Therapeutics for Neovascular Eye Disease, ACS Chem. Biol. 2017, 12, 825-832.

The invention claimed is:
1. A compound of Formula (I):

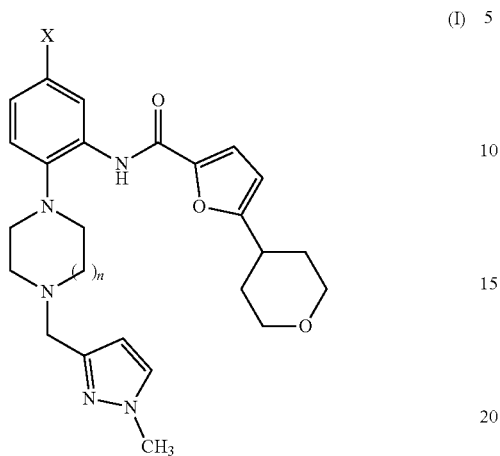

or a pharmaceutically acceptable salt, solvate, hydrate or prodrug thereof; wherein:
X=CF$_3$ and
n=1.

2. A pharmaceutical composition comprising a compound of claim 1, optionally one or more other active ingredients and a pharmaceutically acceptable carrier.

3. The pharmaceutical composition of claim 2, wherein the composition is in a form for topical administration to the eye.

* * * * *